United States Patent
Duty et al.

(10) Patent No.: US 9,868,899 B2
(45) Date of Patent: Jan. 16, 2018

(54) METHOD OF MICROBIALLY PRODUCING METAL GALLATE SPINEL NANO-OBJECTS, AND COMPOSITIONS PRODUCED THEREBY

(71) Applicant: UT-BATTELLE, LLC, Oak Ridge, TN (US)

(72) Inventors: Chad E. Duty, Knoxville, TN (US); Gerald E. Jellison, Jr., Oak Ridge, TN (US); Lonnie J. Love, Knoxville, TN (US); Ji Won Moon, Oak Ridge, TN (US); Tommy J. Phelps, Knoxville, TN (US); Ilia N. Ivanov, Knoxville, TN (US); Jongsu Kim, Busan (KR); Jehong Park, Busan (KR); Robert Lauf, Oak Ridge, TN (US)

(73) Assignee: UT-BATTELLE, LLC, Oak Ridge, TN (US)

(*) Notice: Subject to any disclaimer, the term of this patent is extended or adjusted under 35 U.S.C. 154(b) by 527 days.

(21) Appl. No.: 14/399,679

(22) PCT Filed: Mar. 14, 2013

(86) PCT No.: PCT/US2013/031357
§ 371 (c)(1),
(2) Date: Nov. 7, 2014

(87) PCT Pub. No.: WO2013/169364
PCT Pub. Date: Nov. 14, 2013

(65) Prior Publication Data
US 2015/0118519 A1 Apr. 30, 2015

Related U.S. Application Data

(60) Provisional application No. 61/644,211, filed on May 8, 2012.

(51) Int. Cl.
*C01G 15/00* (2006.01)
*G01C 9/00* (2006.01)
(Continued)

(52) U.S. Cl.
CPC .......... *C09K 11/7728* (2013.01); *C01G 15/00* (2013.01); *C01G 15/006* (2013.01);
(Continued)

(58) Field of Classification Search
CPC .. C01G 15/006; C01G 15/00; C09K 11/7728; C09K 11/77; C09K 11/68; C09K 11/62
See application file for complete search history.

(56) References Cited

U.S. PATENT DOCUMENTS 7,312,575 B2 * 12/2007 Zeng ................... C09K 11/623
                                                                 313/582
7,956,346 B2 *  6/2011 Iwasaki ................ H01L 33/16
                                                                 257/13

(Continued)

*Primary Examiner* — C Melissa Koslow
(74) *Attorney, Agent, or Firm* — Scully Scott Murphy & Presser

(57) ABSTRACT

A method of forming a metal gallate spinel structure that includes mixing a divalent metal-containing salt and a gallium-containing salt in solution with fermentative or thermophilic bacteria. In the process, the bacteria nucleate metal gallate spinel nano-objects from the divalent metal-containing salt and the gallium-containing salt without requiring reduction of a metal in the solution. The metal gallate spinel structures, as well as light-emitting structures in which they are incorporated, are also described.

36 Claims, 21 Drawing Sheets

(51) Int. Cl.
*C12P 3/00* (2006.01)
*C30B 29/26* (2006.01)
*C09K 11/08* (2006.01)
*C09K 11/54* (2006.01)
*C09K 11/57* (2006.01)
*C09K 11/60* (2006.01)
*C09K 11/62* (2006.01)
*C09K 11/68* (2006.01)
*C09K 11/77* (2006.01)
*C09K 11/64* (2006.01)
*C09K 11/65* (2006.01)
*H01L 33/50* (2010.01)

(52) U.S. Cl.
CPC .......... *C09K 11/621* (2013.01); *C09K 11/623* (2013.01); *C09K 11/642* (2013.01); *C09K 11/65* (2013.01); *C09K 11/682* (2013.01); *C09K 11/7702* (2013.01); *C09K 11/773* (2013.01); *C12P 3/00* (2013.01); *C01P 2002/32* (2013.01); *C01P 2002/52* (2013.01); *C01P 2002/72* (2013.01); *C01P 2002/84* (2013.01); *C30B 29/26* (2013.01); *H01L 33/504* (2013.01)

(56) References Cited

U.S. PATENT DOCUMENTS

2010/0184179 A1* 7/2010 Rondinone .............. B82Y 5/00
  435/168
2010/0193752 A1* 8/2010 Phelps ..................... C12P 3/00
  252/519.4

* cited by examiner

METHOD OF MICROBIALLY PRODUCING METAL GALLATE SPINEL NANO-OBJECTS, AND COMPOSITIONS PRODUCED THEREBY

CROSS-REFERENCE TO RELATED APPLICATIONS

This application claims the benefit of priority from U.S. Provisional Application No. 61/644,211, filed on May 8, 2012, which is herein incorporated by reference in its entirety.

STATEMENT REGARDING FEDERALLY SPONSORED RESEARCH

This invention was made with government support under Contract Number DE-AC05-00OR22725 between the United States Department of Energy and UT-Battelle, LLC. The U.S. government has certain rights in this invention.

FIELD OF THE INVENTION

The present disclosure relates to luminescent materials, and more particularly relates to the production of luminescent materials using fermentation type processes.

BACKGROUND

Conventional incandescent bulb design is not energy efficient. In some instances, 98% of the energy input to incandescent bulbs ends up as heat instead of light. Energy conversion to visible light for fluorescent lighting technology is much higher, e.g., 10% to 15%. However, their design requires mercury, which is toxic to the environment, thereby posing a problem for recycling of these lamps. Thus, there are ongoing efforts in finding new materials having luminescent and phosphorescent properties that can be more environmentally friendly while remaining cost effective and amenable to scaled up production.

SUMMARY OF THE INVENTION

In one embodiment of the present disclosure, a metal gallate spinel structure is provided by mixing a divalent metal-containing salt (e.g., salt of $Cu^{+2}$, $Zn^{+2}$, or $Cd^{+2}$) with a gallium-containing salt in solution with fermentative or thermophilic bacteria under conditions where the bacteria nucleate and grow the divalent metal gallate spinel structure. In particular embodiments, a zinc gallate spinel structure is provided by mixing a zinc-containing salt and a gallium-containing salt in solution with fermentative or thermophilic bacteria under conditions where the bacteria nucleate and grow the zinc gallate spinel structure. The bacteria nucleates a metal gallate spinel structure from the metal-containing salt and the gallium-containing salt without requiring reduction of at least a metal from the mixed salt solution.

In another aspect of the present disclosure, a method of forming a divalent metal gallate spinel structure is provided in which the divalent metal gallate spinel structure is doped to tune an emission wavelength that is provided by the doped divalent metal gallate spinel. In one embodiment, the method of forming the divalent metal gallate spinel structure includes providing a supply of fermentative or thermophilic bacteria and reacting a metal-containing salt and a gallium-containing salt with the supply of bacteria. Treatment of the divalent metal-containing salt and the gallium-containing salt with the thermophilic bacteria nucleates a divalent metal gallate spinel structure. The metal gallate spinel (and particularly, zinc gallate spinel) structure may be doped to tune a wavelength of light emission from the metal gallate spinel structure. The metal gallate spinel structure may then be annealed.

In another aspect of the present disclosure, a method of forming a structure for emitting white light is provided from doped phosphors produced by fermentation of metal-containing salts and gallium-containing salts with fermentative or thermophilic bacteria. In one particular embodiment, the method of forming a white light emitting structure includes forming a first phosphor of a first doped metal gallate spinel (particularly, zinc gallate spinel) structure that is nucleated by a first fermentation with a fermentative or thermophilic bacteria and annealing. The first phosphor emits a first wavelength of red light ranging from 570 nm to 750 nm. A second phosphor of a second doped metal gallate spinel (particularly, zinc gallate spinel) structure may be nucleated during a second fermentation with fermentative or thermophilic bacteria. Following nucleation, the second doped metal gallate spinel (particularly, zinc gallate spinel) structure may be annealed, wherein the second doped metal gallate spinel (particularly, zinc gallate spinel) structure emits a wavelength of green light ranging from 495 nm to 570 nm. A third phosphor of a third metal gallate spinel (particularly, zinc gallate spinel) structure may then be nucleated by a third fermentation with the fermentative or thermophilic bacteria and may be annealed, in which the third phosphor emits a wavelength of violet and blue light ranging from 400 nm to 495 nm. At least the first phosphor, the second phosphor, and the third phosphor may then be mixed to form the structure for emitting the white light.

In yet another aspect of the present disclosure, a white light emitting structure is provided that is composed of a mixture of at least three metal gallate spinel (and particularly, zinc gallate spinel) structures. A first metal gallate spinel (and particularly, zinc gallate spinel) that is doped with chromium or europium provides a red light emitting phosphor. A second metal gallate spinel (and particularly, zinc gallate spinel) that is doped with manganese provides a green light emitting phosphor. A third metal gallate spinel (and particularly, zinc gallate spinel) provides a blue light emitting phosphor. The first, second, and third phosphor are homogeneously distributed on a transparent substrate.

BRIEF DESCRIPTION OF THE DRAWINGS

The following detailed description, given by way of example and not intended to limit the disclosure solely thereto, will best be appreciated in conjunction with the accompanying drawings, wherein like reference numerals denote like elements and parts, in which.

DETAILED DESCRIPTION

Figure 1A:
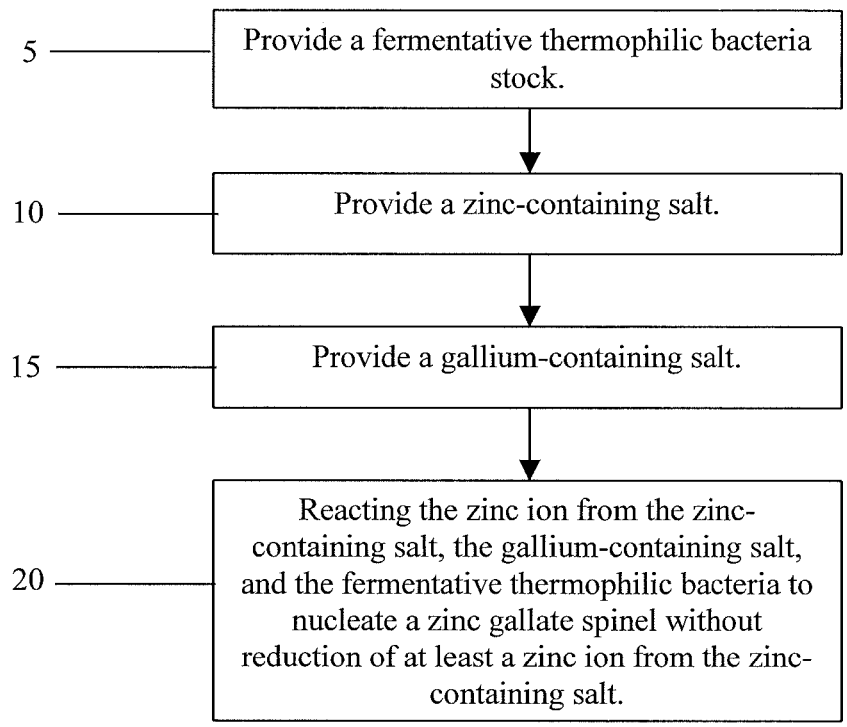
FIG. 1A is a process diagram illustrating a method of nucleating a zinc gallate spinel structure with fermentative or thermophilic bacteria without requiring reduction of at least a metal-containing salt, in accordance with one embodiment of the present disclosure.

Detailed embodiments of the present disclosure are described herein; however, it is to be understood that the disclosed embodiments are merely illustrative of the compositions, structures and methods of the disclosure that may be embodied in various forms. In addition, the examples given in connection with the various embodiments are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the compositions, structures and methods disclosed herein. References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment.

Referring to FIG. 1, in one embodiment, the present disclosure provides a method of nucleating divalent metal (particularly zinc) gallate spinel structures from divalent metal-containing salts and gallium-containing salts with fermentative or thermophilic bacteria. The method disclosed herein may be referred to as nanofermentation of the divalent metal gallate spinel structures. Nanofermentation is a process of microbially induced, i.e., induced by fermentative or thermophilic bacteria, using microbial activity as the driving force for nucleating divalent metal gallate spinel structures on or adjacent to the cell wall of the fermentative or thermophilic bacteria by adjusting the pH and reduction potential ($E_h$) of the micro environment adjacent to the fermentative or thermophilic bacteria.

A spinel structure is a mineral of the formula $A^{2+}B_2^{3+}O_4^{2-}$, which crystallizes in the cubic (isometric) crystal system, with the oxide anions arranged in a cubic close-packed lattice and the cations A and B occupying some or all of the tetrahedral and octahedral sites in the lattice. In general, A and B can be divalent, trivalent, or quadrivalent cations. In the divalent metal gallate structures considered herein, A can be any divalent metal species, and B is $Ga^{3+}$. The divalent metal species can be, for example, an alkaline earth metal (e.g., $Mg^{2+}$, $Ca^{2+}$, $Sr^{2+}$, or $Ba^{2+}$, or a combination thereof) or a transition metal (e.g., $Mn^{2+}$, $Fe^{2+}$, $Co^{2+}$, $Ni^{2+}$, $Cu^{2+}$, $Zn^{2+}$, or $Cd^{2+}$, or a combination thereof).

In some embodiments of the divalent metal gallate structure $A^{2+}B_2^{3+}O_4^{2-}$, A contains two or more divalent metal species (which may be denoted as A and A'), such as any two of the exemplary divalent metal species provided above. In such compositions, the divalent metal gallate structure could have the generic formula $A_xA'_{1-x}Ga_2O_4$, wherein A' is selected from any of the divalent metals provided for A, and the subscript x is greater than 0 and less than 1, e.g., 0.01, 0.02, 0.05, 0.1, 0.2, 0.3, 0.4, 0.5, 0.6, 0.7, 0.8, 0.9, 0.95, 0.98, or 0.99, or a value within a range bounded by any two of the foregoing values. Some examples of such compositions include the sub-generic formulas $Zn_xCu_{1-x}Ga_2O_4$, $Zn_xCd_{1-x}Ga_2O_4$, $Cu_xCd_{1-x}Ga_2O_4$, $Sr_xZn_{1-x}Ga_2O_4$, $Sr_xCu_{1-x}Ga_2O_4$, $Sr_xCd_{1-x}Ga_2O_4$, and $Ba_xSr_{1-x}Ga_2O_4$, wherein possible values for x have been provided above.

In some embodiments, A includes only divalent metal species, as described above. In other embodiments, A may include, in addition to one or more divalent metals, one or more monovalent metals and/or one or more trivalent metals. Some examples of monovalent metals include the alkali metals (e.g., $Li^+$, $Na^+$, $K^+$, $Rb^+$, and $Cs^+$) as well as some transition and main groups metals (e.g., $Cu^+$, $Ag^+$, and $Tl^+$). Some examples of trivalent metals include the main group metals (e.g., $B^{3+}$, $Al^{3+}$, $Ga^{3+}$, $In^{3+}$, $As^{3+}$, $Sb^{3+}$, and $Bi^{3+}$), transition metals (e.g., $Sc^{3+}$, $V^{3+}$, $Cr^{3+}$, $Mn^{3+}$, $Fe^{3+}$, $Co^{3+}$, $Ni^{3+}$, and $Y^{3+}$), and lanthanide metals (e.g., $La^{3+}$, $Ce^{3+}$, $Pr^{3+}$, $Sm^{3+}$, $Eu^{3+}$, $Gd^{3+}$, $Tb^{3+}$, and $Dy^{3+}$). In the case where monovalent and/or trivalent metals are included, A and A' in the generic or specific gallate spinel compositions above can be independently selected from one or more monovalent, divalent, and trivalent metals, provided that A contains at least one divalent metal. Some examples of metal gallate compositions that include either a monovalent or trivalent metal include $Li_{0.05}Zn_{0.975}Ga_2O_4$, $Al_{0.01}Zn_{0.985}Ga_2O_4$, and $Cu^+_{0.05}Cu^{2+}_{0.975}Ga_2O_4$. In some embodiments, any of the foregoing monovalent and/or trivalent metals may be included as dopants into the metal gallate structure.

The metal gallate (and particularly, zinc gallate) spinel structures that are formed in accordance with the present disclosure are nucleated in a solution with fermentative or thermophilic bacteria and are not produced by reduction reactions. In some embodiments, microbial reduction (decrease redox potential) is employed to achieve the appropriate $pH-E_h$ regime suitable spinel structure formation, such as zinc gallate phosphor structures. The term "nucleation", "nucleating", and "nucleate" as used herein to describe the formation of spinel structures mean that solute molecules dispersed in a solvent gather into clusters, on the nanometer scale (elevating solute concentration in a small region) and become stable. These stable clusters constitute the nuclei. When the clusters are not stable, they redissolve. The nucelation of the divalent metal gallate spinel structures in the solution of fermentative or thermophilic bacteria that are disclosed herein does not require the reduction of any metal and non-metal components in the target nanoparticles.

Redox (reduction-oxidation) reactions describe all chemical reactions in which atoms have their oxidation state changed. A "reduction reaction" is the gain of electrons or a decrease in oxidation state by a molecule, atom, or ion. One example of a redution reaction is the formation of magnetite spinel ($Fe_3O_4$) as in the following reaction:

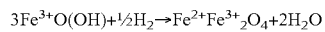

In the above reaction, Fe(III) is reduced to Fe(II). Another example of a reduction reaction is the formation of semiconducting material (CdS) as in the following reaction:

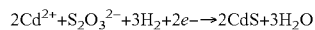

In the above reaction S(IV) is reduced to S(−II). In comparison to the above example of a reduction reaction, the zinc gallate spinel structure produced using the thermophilic bacteria of the present disclosure does not include reduction of a metal ion, e.g., Zn. For example, a zinc gallate structure nucleated at neutral pH in accordance with the present disclosure may be as follows:

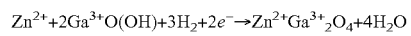

Figure 1B:
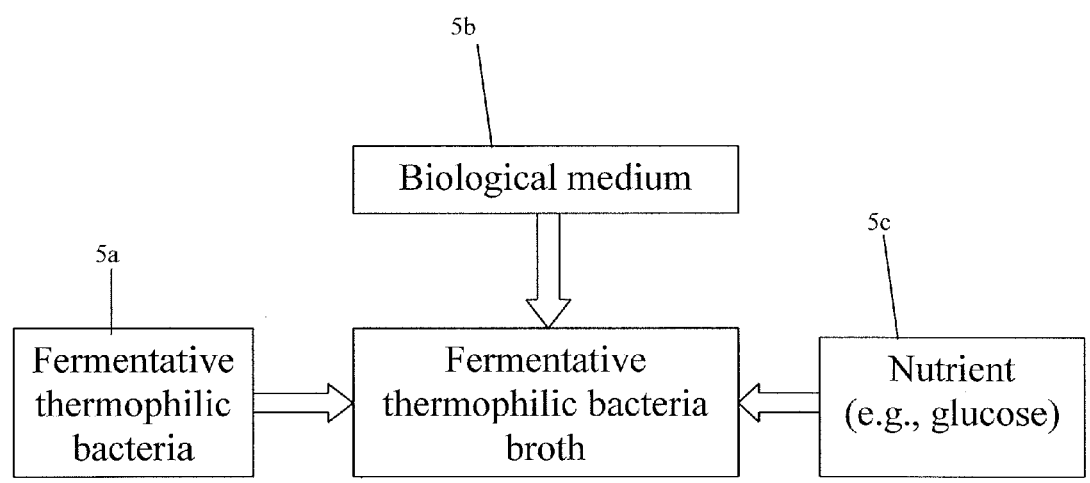
FIG. 1B is a process diagram illustrating one embodiment of providing the bacterial broth of step 5 of the process diagram depicted in FIG. 1A.

Referring to FIG. 1A, in one embodiment, the method of nucleating metal gallate (and particularly, zinc gallate) spinel structures may begin at step 5 with providing fermentative or thermophilic bacterial broth. The term "fermentative bacteria", as used herein, refers to bacteria that obtain electrons from an electron donor (e.g. glucose) and then release electrons extracellularly, thereby resulting in the production of carbon dioxide, alcohol, and organic acids under anaerobic conditions. The term "thermophilic bacteria", as used herein, refers to bacteria that survive at temperatures above 45° C. (113° F.). In some examples, thermophilic bacteria live at or even above the boiling point of water. Strains of thermophilic bacteria have been identified with optimum temperatures ranging from 55° C. to 105° C. (above the boiling point of water), and many temperatures in between. Thermophilic bacteria occur naturally in hot springs, tropical soils, compost heaps, etc. In one embodiment, step 5 the bacterial broth that is depicted in FIG. 1A may include the steps of the process sequence that is depicted in FIG. 1B. FIG. 1B illustrates that forming the fermentative or thermophilic bacteria may include the steps of providing a bacterial stock 5a, providing a biological medium 5b and providing a nutrient, e.g., glucose 5c. The fermentative or thermophilic bacteria considered herein are primarily those that can adjust the microenvironment around the cell to lower the $E_h$ (e.g., to −100 mV, −200 mV, −300 mV, or −350 mV), and that preferably survive or thrive around neutral pH (e.g., 4-10). The bacteria are also preferably less prone to inactivation from metal toxicity under high metal concentrations. In some embodiments, the bacteria are both fermentative and thermophilic, i.e., "fermentative thermophilic bacteria".

In one embodiment, the bacterial stock may be a species of *Thermoanaerobacter* bacteria. A particular species of *Thermoanaerobacter* considered herein is *Thermoanaerobacter* strain TOR-39, a sample of which was deposited with the American Type Culture Collection (10801 University Blvd., Manassas, Va. 20010) on Sep. 7, 2001 as accession number PTA-3695. Strain TOR-39 is a thermophile that grows optimally at temperatures from 60° C. to 70° C. The conditions needed to grow and maintain this strain, including basal medium, nutrients, vitamins, and trace elements are detailed in U.S. Pat. No. 6,444,453, the entire contents of which are incorporated herein by reference. Some particular strains of *Thermoanaerobacter ethanolicus* particularly considered herein include *T. ethanolicus* strain C1 and *T. ethanolicus* strain M3. Some other bacterial species of this class include *Thermoanaerobacter* X513, X514, and X561 (as described in Roh et al., *Applied and Environmental Microbiology*, December 2002, pp. 6013-6020) and *Thermoanaerobacter* OB47 (Hamilton-Brehm et al., *Applied and Environmental Microbiology*, February 2010, pp. 1014-1020).

Another group of bacteria particularly considered herein is the class Thermococci. An order of Thermococci particularly considered herein is Thermococcales. A family of Thermococcales particularly considered herein is Thermococcaceae. A genus of Thermococcaceae particularly considered herein is *Thermococcus*. A species of *Thermococcus* particularly considered herein is *Thermococcus litoralis*.

Another group of bacteria particularly considered herein is the genus *Thermoterrabacterium*. A species of *Thermoterrabacterium* particularly considered herein is *Thermoterrabacterium ferrireducens*, and particularly, strain JW/AS-Y7.

Still another group of bacteria particularly considered herein is the phylum Deinococcus-Thermus. A class of Deinococcus-Thermus particularly considered herein is Deinococci. An order of Deinococci particularly considered herein is Thermales. A genus of Thermales particularly considered herein is *Thermus*. A species of *Thermus* particularly considered herein is *Thermus* sp. strain SA-01.

Other bacteria particularly considered herein include thermophilic species within any of the genera *Thermoanaerobacterium* (e.g., *T. thermosulfurigenes, T. polysaccharolyticum, T. zeae, T. aciditolerans*, and *T. aotearoense*), *Bacillus* (e.g., *B. infernus*), *Clostridium* (e.g., *C. thermocellum*), *Anaerocellum* (e.g., *A. thermophilum*), *Dictyoglomus* (e.g., *D. thermophilum*), and *Caldicellulosiruptor* (e.g., *C. acetigenus, C. hydrothermalis, C. kristjanssonii, C. kronotskiensis, C. lactoaceticus, C. owensensis*, and *C. saccharolyticus*).

It is noted that the above examples of fermentative or thermophilic bacteria are provided for illustrative purposes only and are not intended to limit the present disclosure to only the types of bacteria that are described above. For example, embodiments have been contemplated in which the bacteria being employed for forming metal (particularly, zinc) gallate spinel structures are mesophilic (20-45° C.) or psychrophilic (less than 20° C.).

The culture medium, i.e., biological medium 5b, for sustaining the fermentative or thermophilic bacteria, can be an aqueous-based medium. The culture medium may also facilitate growth of the bacteria. In one embodiment, an anaerobic culture vessel is provided that contains the aqueous-based medium in which the bacteria are grown anaerobically. Additives such as electron donors, vitamins, trace elements, and other nutrients are included in the culture medium. An electron donor is any compound or material capable of being oxidatively consumed by the bacteria such that donatable electrons are provided to the bacteria by the consumption process.

In one embodiment, the electron donor, e.g., nutrient 5c, includes one or more carboxylate-containing compounds that can be oxidatively consumed by the fermentative or thermophilic bacteria. Some examples of suitable carboxylate-containing compounds include formate, acetate, propionate, butyrate, oxalate, malonate, succinate, fumarate, glutarate, lactate, pyruvate, glyoxylate, glycolate, and citrate.

In another embodiment, the electron donor includes one or more sugars (i.e., saccharides, disaccharides, oligosaccharides, or polysaccharides) that can be oxidatively consumed by the fermentative or thermophilic bacteria. Some examples of suitable sugars include glucose, fructose, sucrose, galactose, maltose, mannose, arabinose, xylose, lactose, and disaccharides therefrom, oligosaccharides therefrom, or polysaccharides therefrom.

In another embodiment, the electron donor includes one or more inorganic species that can be oxidatively consumed by the fermentative or thermophilic bacteria. The inorganic species can be, for example, an oxidizable gas, such as hydrogen. Such gases can be oxidized by hydrogen-consuming microbes, which have the capacity to reduce one or more metals or non-metal compounds by the produced electrons. It is noted that the above electron donors are purely exemplary and not intended to limit the present disclosure to any of the materials and concentrations described herein. In some embodiments, and one or more classes or specific types of electron donors are excluded from the process.

In one embodiment, the concentration of electron donor within an aqueous-based medium that provides the culture medium for the fermentative or thermophilic bacteria ranges from 1.0 mM to 20 mM. In another embodiment, the concentration of electron donor within the an aqueous-based media that provides the culture medium for the fermentative or thermophilic bacteria ranges from 0.4 mM to 1.0 mM. In yet another embodiment, the concentration of electron donor within the an aqueous-based media that provides the culture medium for the fermentative or thermophilic bacteria ranges from 0.5 mM to 1.5 mM. Example concentrations for the electron donor within the aqueous-based media that provides the culture medium for the fermentative or thermophilic bacteria include 0.4 mM, 0.5 mM, 0.6 mM, 1.0 mM, 1.5 mM, 4, mM, 6 mM and 20 mM. Any range resulting from any two of the foregoing values is also contemplated herein.

In one embodiment, the method of nucleating metal gallate (and particularly, zinc gallate) spinel structures with fermentative or thermophilic bacteria includes providing at least one divalent metal-containing (or zinc-containing) salt (and optionally, one or more monovalent or trivalent metal-containing salts) at step 10 of the process sequence depicted in FIG. 1A. The divalent metal-containing salt may be any ionic compound that dissociates to provide a divalent metal cation, such as $Zn^{2+}$, $Cu^{2+}$, or $Cd^{2+}$. In some embodiments, the divalent metal-containing salt may be a bromide, hydrate, phosphate, stearate, fluoride, acrylate, or combination thereof, of a divalent metal. Some examples of zinc-containing salts include zinc chloride ($ZnCl_2$), zinc bromide ($ZnBr_2$), zinc nitrate hydrate ($Zn(NO_3)_2 \cdot xH_2O$), zinc sulfate hydrate ($ZnSO_4 \cdot xH_2O$), zinc phosphate ($Zn_3(PO_4)_2$), zinc acetate hydrate ($(CH_3CO_2)_2Zn) \cdot xH_2O$), zinc stearate ($[CH_3(CH_2)_{16}COO]_2Zn$), zinc fluoride ($ZnF_2$), zinc iodide ($ZnI_2$), zinc methoxide ($C_2H_6O_2Zn$), zinc acrylate (($H_2C=CHCO_2)_2Zn$), and combinations thereof. Some examples of copper-containing salts include cupric chloride ($CuCl_2$), cuprous chloride (CuCl), cupric bromide ($CuBr_2$), cuprous bromide (CuBr), cupric nitrate ($Cu(NO_3)_2 \cdot xH_2O$), and cupric sulfate ($CuSO_4 \cdot xH_2O$), where x may be 0 or an integer of at least one. Some examples of cadmium-containing salts include cadmium chloride ($CdCl_2$), cadmium bromide ($CdBr_2$), cadmium nitrate ($Cd(NO_3)_2 \cdot xH_2O$), and cadmium sulfate ($CuSO_4 \cdot xH_2O$), where x may be 0 or an integer of at least one. Some examples of monovalent metal-containing salts include compounds of the formula $M_v X^{-m}{}_w$, wherein M is a monovalent metal (e.g., $Na^+$, $K^+$, $Rb^+$, $Cs^+$, $Cu^+$, $Ag^+$, or $Tl^+$), X is a negatively charged group (with oxidation state $-m$), such as, for example, a halide (e.g., $F^-$, $Cl^-$, $Br^-$, or $I^-$), hydroxide, alkoxide, carbonate, sulfate, sulfite, nitrate, nitrite, phosphate, acrylate, or stearate group, and v and w subscripts are integers, such that $v = m \times w$. Some examples of trivalent metal-containing salts include compounds of the formula $M'_v X^{-m}{}_w$, wherein M is a trivalent metal, such as any of the trivalent metal species provided above, X is a negatively charged group (with oxidation state $-m$), such as any of the negatively charged groups provided above, and v and w subscripts are integers, such that $3v = m \times w$.

It is noted that the above description of monovalent, divalent, and trivalent metal-containing salts is provided for illustrative purposes only, and is not intended to limit the present disclosure, as other such metal-containing salts are suitable for use with the methods disclosed herein. For example, any metal-containing salt is suitable for use with the methods and compositions of the present disclosure, so long as the metal-containing salt is capable of forming a metal gallate spinel structure that is nucleated with fermentative or thermophilic bacteria without reduction of the metal.

In one embodiment, the method of nucleating metal gallate spinel structures with fermentative or thermophilic bacteria includes providing at least one gallium-containing salt at step 15 of the process sequence depicted in FIG. 1A. The gallium-containing salt may be any ionic compound that dissociates to provide a gallium cation, e.g., $Ga^{3+}$. In some embodiments, the gallium-containing salt may be a chloride, hydroxide, bromide, fluoride, iodide, or combination thereof, of gallium. In some examples, the gallium-containing salt may include at least one gallium-containing salt selected from the group consisting of gallium chloride (e.g., $GaCl_3$ or $GaCl_2$), gallium nitrate hydrate ($GaNO_3.xH_2O$), gallium fluoride ($GaF_3$), gallium iodide ($GaI_3$), gallium bromide ($GaBr_3$), gallium sulfate hydrate ($GaSO_4.xH_2O$), and combinations thereof. It is noted that the above description of gallium-containing salts is provided for illustrative purposes only, and is not intended to limit the present disclosure, as other gallium-containing salts are suitable for use with the methods disclosed herein. For example, any gallium-containing salt is suitable for use with the methods and compositions of the present disclosure, so long as the gallium-containing salt is capable of forming a divalent metal gallate spinel structure that is nucleated with fermentative or thermophilic bacteria without reduction of the gallium.

The divalent metal-containing salt, gallium-containing salt, electron donor, and the fermentative or thermophilic bacteria are then combined to nucleate a divalent metal gallate spinel without reduction of at least a divalent metal ion from the metal-containing salt as step 20 of the process sequence that is depicted in FIG. 1A. In some embodiments, the divalent metal-containing salt, the gallium-containing salt and the fermentative or thermophilic bacteria, including the culture media (e.g., the electron donors, vitamins, trace elements, and other nutrients included in the culture medium), are mixed in a suitable container and subjected to conditions (e.g., temperature, pH, and reaction time) suitable for producing a metal gallate spinel structure from the reaction components. In one embodiment, the container for holding the reaction components is simple by containing no more than container walls, a bottom, and a lid. In another embodiment, the container is more complex by including additional features, such as inlet and outlet elements for gases, liquids, or solids, one or more heating elements, nanoparticle separation features (e.g., traps or magnets), one or more agitating elements, fluid recirculating elements, electronic controls for controlling one or more of these or other conditions, and so on.

Figure 2:
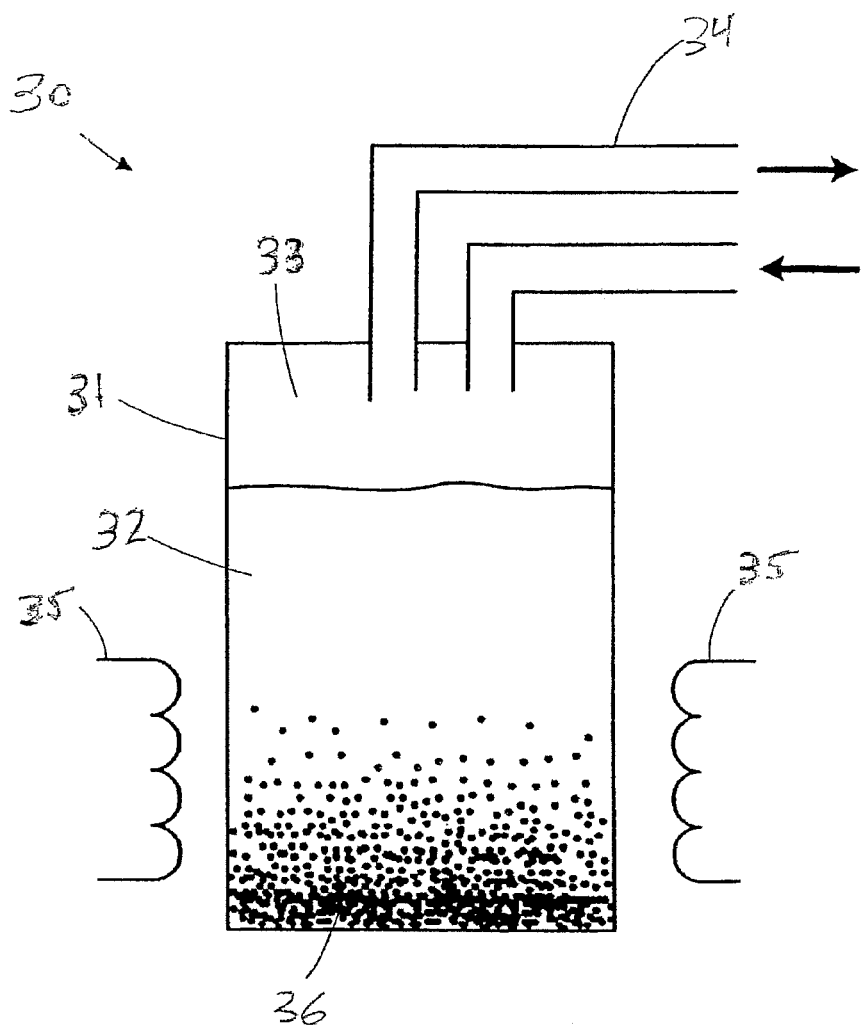
FIG. 2 is a side cross-sectional schematic view of a batch type reactor used for nucleating a zinc gallate spinel structure with fermentative or thermophilic bacteria, in accordance with the present disclosure.

FIG. 2 is one embodiment of a simplified diagram of a batch type reactor 30 suitable for carrying out the inventive process shown in FIG. 1A. The reactor includes a container 31 constructed of glass or other inert material. A culture medium 32 is introduced in the container 31. The culture medium 32 may contain an aqueous solution of the fermentative or thermophilic bacteria, electron donors, nutrients, vitamins, trace elements, vitamins, and other compounds as described in the foregoing examples. The container 31 is sealed to prevent the entry of air into the headspace gas region 33 thereby maintaining anaerobic conditions within the culture, as well as permitting the inventive process to be carried out at pressures greater or less than ambient if desired. A gas conduit 34 is included to allow the introduction of selected gases into the container 31 and to allow gases to exit the container 31. An electron donor is introduced into the culture either as a gas (such as hydrogen along with a relatively inert diluent or carrier gas such as $N_2$, Ar, He, $CO_2$) through the gas conduit 34, or dissolved directly into the culture medium 34 in the case of simple organics, such as glucose, lactate, and pyruvate. The zinc-containing salt and the gallium-containing salt may be introduced to the culture medium 32 including the fermentative or thermophilic bacteria.

In one embodiment, the divalent metal-containing salt is present in the aqueous solution with the fermentative or thermophilic bacteria in a concentration ranging from 0.01 mM to 10 mM. In another embodiment, the divalent metal-containing salt is present in the aqueous solution with the fermentative or thermophilic bacteria in a concentration ranging from 1.5 mM to 3 mM. In yet another embodiment, the divalent metal-containing salt is present in the aqueous solution with the fermentative or thermophilic bacteria in a concentration ranging from 1.8 mM to 2.1 mM. Some exemplary concentrations for the divalent metal-containing salt present in the aqueous solution may include 1.88 mM, 1.92 mM, 1.96 mM, 1.98 mM and 2 mM.

In one embodiment, the gallium-containing salt is present in the aqueous solution with the fermentative or thermophilic bacteria in a concentration ranging from 0.02 mM to 20 mM. In another embodiment, the gallium-containing salt is present in the aqueous solution with the fermentative or thermophilic bacteria in a concentration ranging from 3 mM to 5 mM. In yet another embodiment, the gallium-containing salt is present in the aqueous solution with the fermentative or thermophilic bacteria in a concentration ranging from 3.75 mM to 4 mM. Some exemplary concentrations for the gallium-containing salt present in the aqueous solution may include 3.6 mM, 3.76 mM, 3.8 mM, 3.84 mM, 3.92 mM, 3.96 mM and 4 mM.

The fermentative or thermophilic bacteria, the metal-containing salt, and the gallium-containing salt, as well as other additives employed in the formation of the divalent metal gallate structure, may be combined in any suitable manner in the batch reactor 30. For example, each of the above-referenced reaction components or a combination thereof may be prepared before the components are combined, or alternatively, obtained in a pre-packaged form before the components are combined. When components or combinations thereof are provided in package form, the packaged forms may be designed to be used in their entireties, or alternatively, designed such that a portion of each is used (e.g., as aliquots of a concentrate). In some embodiments, the order of addition of components has essentially no bearing on the final compositional and physical characteristics of the produced divalent metal gallate spinel structures. In other embodiments, the compositional and/or physical characteristics of the resulting divalent metal gallate spinel structures are affected in some way by the order in which components are combined.

Referring to FIG. 2, a heating element 35 existing inside and/or outside of container 31 is provided proximate the container 31 to maintain the culture medium 32 at a desired temperature for growth of the fermentative or thermophilic bacteria. When fermentative or thermophilic bacteria are used in aqueous solution with the metal-containing salt and gallium-containing salt, the temperature at which the reaction is conducted can be at least, for example, 40° C., 45° C., 50° C., 55° C., 60° C., 65° C., 70° C., 75° C., 80° C., 85° C., or 90° C., depending on the type of microbes being used.

Any range resulting from any two of the foregoing values is also contemplated herein. When mesophilic bacteria are used, the temperature can be at least 15° C., 20° C., 25° C., or 30° C., and up to any of the temperatures given above for the fermentative or thermophilic bacteria. When psychrophilic bacteria are used, the temperature at which the reaction is conducted can be less than, for example, 40° C., or at or less than 35° C., 30° C., 25° C., 20° C., 15° C., 10° C., 5° C., 0° C., or −5° C., or any range resulting from any two of the foregoing values. In one example, when employing *Thermoanaerobacter* sp. strain TOR-39, the temperature is preferably maintained between 45° C. and 75° C.

In some embodiments, the fermentative or thermophilic bacteria function as nucleating agents or templates in the crystallization of the spinel structure for the metal-containing salt, the gallium-containing salt, and the water component of the aqueous solution. Without being bound by any theory, it is believed that the fermentative or thermophilic bacteria are organizing the salts, i.e., metal-containing salt and gallium-containing salt, and the water into the $A^{2+}B_2^{3+}O_4^2$ crystal spinel structure of the divalent metal gallate spinel. As indicated above, the nucleation of the divalent metal gallate structure from the divalent metal-containing salt and the gallium-containing salt in the aqueous solution with the fermentative or thermophilic bacteria is not a reduction reaction.

To precipitate the divalent metal gallate spinel structure from the aqueous solution with the fermentative or thermophilic bacteria, the pH of the aqueous solution containing the metal-containing salt and the gallium-containing salt is adjusted to range from 5.0 to 9.0 when residing in container 31. In another embodiment, to precipitate the divalent metal gallate spinel structure from the aqueous solution with the fermentative or thermophilic bacteria, the pH of the aqueous solution containing the divalent metal-containing salt and the gallium-containing salt is adjusted to range from 5.5 to 8.5. In yet another embodiment, to precipitate the divalent metal gallate spinel structure from the aqueous solution with the fermentative or thermophilic bacteria, the pH of the aqueous solution containing the divalent metal-containing salt and the gallium-containing salt is adjusted to range from 6.0 to 8.0. In an even further embodiment, to precipitate the divalent metal gallate spinel structure from the aqueous solution with the fermentative or thermophilic bacteria, the pH of the aqueous solution containing the divalent metal-containing salt and the gallium-containing salt is adjusted to range from 6.5 to 8.0. In some examples, the divalent metal gallate spinel structures may be precipitated from an aqueous solution of divalent metal-containing salt and gallium-containing salt in the presence of fermentative or thermophilic bacteria, in which the pH of the aqueous solution is 6.41, 6.42, 6.43, 7.57, 7.60 or 7.61. Moreover, the pH of the aqueous solution may be adjusted with one or more pH buffers. Some examples of buffers include sodium hydroxide, potassium hydroxide, hydrochloric acid, N-(2-hydroxyethyl)piperazine-N'-(2-ethanesulfonic acid) (HEPES), N-(2-hydroxyethyl)piperazine-N'-(2-ethanesulfonic acid) sodium salt (HEPES sodium salt), 3-(N-morpholino)propanesulfonic acid (MOPS),3-(N-morpholino)propanesulfonic acid sodium salt (MOPS sodium salt), and other buffers commonly used in biological research as provided in Good et al., 1966, Biochemistry 5:467-477.

To precipitate the divalent metal gallate spinel structure from the aqueous solution with the fermentative or thermophilic bacteria, the reduction potential ($E_h$) of the aqueous solution containing the divalent metal-containing salt and the gallium-containing salt is preferably adjusted to be within the range of 100 mV to −350 mV. In one embodiment, to precipitate the divalent metal gallate spinel structure from the aqueous solution with the fermentative or thermophilic bacteria, the reduction potential ($E_h$) of the aqueous solution containing the divalent metal-containing salt and the gallium-containing salt is adjusted to be within the range of 50 mV to −250 mV. In another embodiment, to precipitate the divalent metal gallate spinel structure from the aqueous solution with the fermentative or thermophilic bacteria, the reduction potential ($E_h$) of the aqueous solution containing the divalent metal-containing salt and the gallium-containing salt is adjusted to be within the range of 0 mV to −150 mV. In yet another embodiment, to precipitate the divalent metal gallate spinel structure from the aqueous solution with the fermentative or thermophilic bacteria, the reduction potential ($E_h$) of the aqueous solution containing the divalent metal-containing salt and the gallium-containing salt is adjusted to be within the range of −100 mV to −145 mV. In some examples, the divalent metal gallate spinel structures may be precipitated from an aqueous solution of divalent metal-containing salt and gallium-containing salt in the presence of fermentative or thermophilic bacteria, in which the reduction potential ($E_h$) of the aqueous solution is −110 mV, −111 mV, −119 mV, −137 mV, −138 mV or −142 mV. The reduction potential ($E_h$) of the aqueous solution may be adjusted by adjusting the electron donors, microbial activity, reducing agents (e.g. cysteine), or addition of external current (e.g. direct current) in the aqueous solution.

A divalent metal gallate spinel structure forms in the container 32 as the bacteria nucleates the spinel structure from the divalent metal-containing salt, the gallium-containing salt, and the water component of the aqueous solution. As the crystal size of the spinel structures increases, the divalent metal gallate spinel structures precipitate from solution. In some embodiments, the divalent metal gallate spinel is a zinc gallate spinel structure of the composition $ZnGa_2O_4$. In other embodiments, the divalent metal gallate spinel is a copper gallate spinel structure of the composition $CuGa_2O_4$. In other embodiments, the divalent metal gallate spinel is a cadmium gallate spinel structure of the composition $CdGa_2O_4$. The relative molar ratio of the divalent metal may diverge from 1, and the relative molar ratio of Ga may diverge from 2 when 0 is set to 4.

The divalent metal gallate spinel objects that precipitate from the aqueous solution containing the fermentative or thermophilic bacteria, the divalent metal-containing salt, and the gallium-containing salt preferably have a largest dimensional axis of 1 micron or less. The spinel structures disclosed herein are generally nano-objects (e.g., nanoparticles), which typically have at least one of their dimensional axes up to 500 nm or less. In different embodiments, the divalent metal gallate spinel structure can have a largest axis ranging 1 nm to 500 nm. For example, the divalent metal gallate spinel structure can have a largest axis of 2 nm, 3 nm, 4 nm, 5 nm, 10 nm, 12 nm, 15 nm, 20 nm, 25 nm, 30 nm, 40 nm, 50 nm, 100 nm, 150 nm, 200 nm, 250 nm, 300 nm, 400 nm, or 500 nm, or any range therebetween (e.g., 1-10 nm, 2-10 nm, 1-20 nm, 2-20 nm, 3-20 nm, 1-500 nm, 5-500 nm, 1-150 nm, or 5-150 nm). In one embodiment, the divalent metal gallate objects are nanoparticles that are fairly disperse in size (e.g., having a size variation of 20%, 30%, 40%, 50%, or greater from a median or mean size). In another embodiment, the nanoparticles are fairly monodisperse in size (e.g., having a size variation of or less than 50%, 40%, 30%, 20%, 10%, 5%, 2%, or 1% from a median or mean size). When the divalent metal gallate spinel structure has a spherical geometry, the largest axis would be the diameter of the divalent metal gallate spinel structure.

Referring to FIG. 2, when a sufficient quantity of divalent metal gallate spinel 36 has been precipitated and allowed to settle to the bottom of the container 31, the culture medium 32 is decanted or siphoned and the precipitated divalent metal gallate spinel 36 is collected and washed. The reaction (incubation) time is the period of time that the combined reaction components are subjected to reaction conditions necessary for producing divalent metal gallate spinel 36. Shorter reaction times (e.g., 1-60 minutes) may be used at elevated temperature conditions, whereas longer reaction times (e.g., 1-7 days, or 1-3 weeks) may be used at lower temperatures to obtain a similar yield of product. Typically, shorter reaction times produce smaller particles than particles produced using longer reaction times under the same conditions. The incubation may be, for example, between 3 and 30 days, depending on the amount and size of the crystalline nanoparticle product desired.

Figure 3:
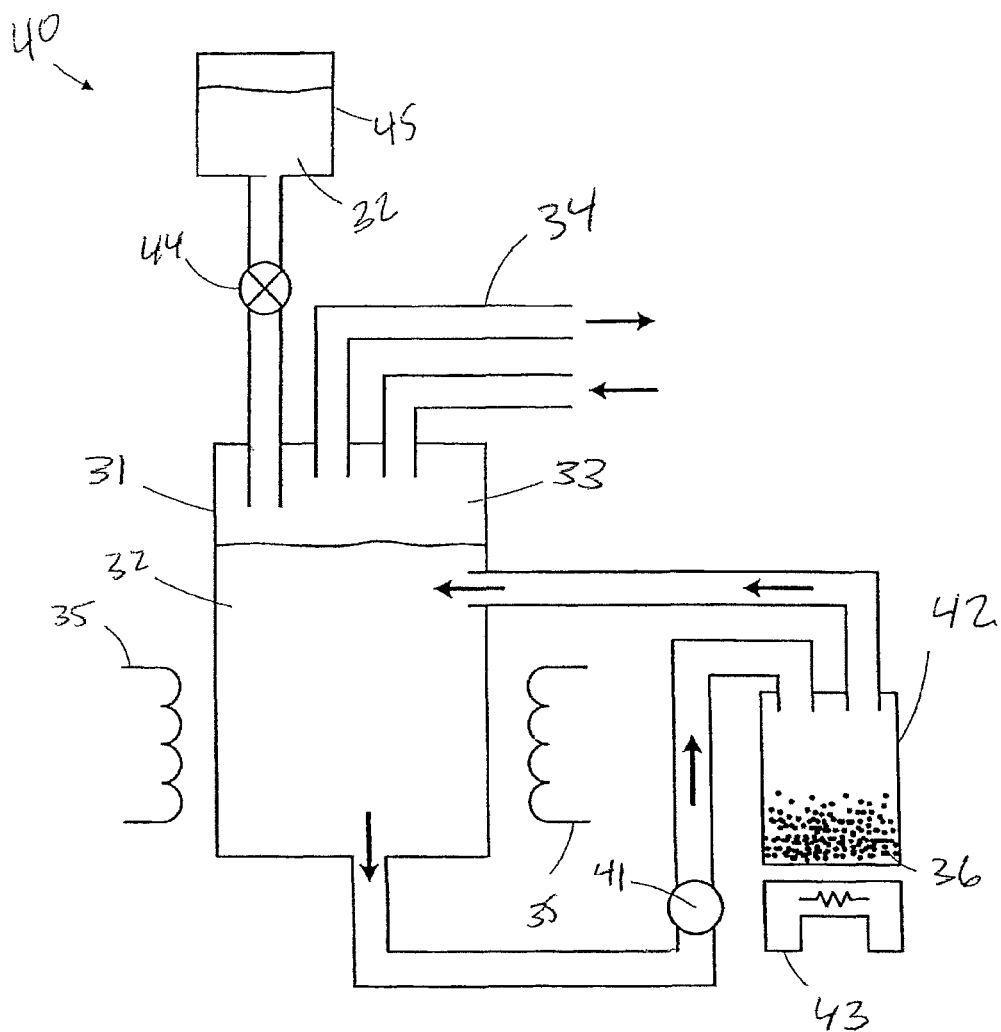
FIG. 3 is a side cross-sectional schematic view of a continuous type reactor used for nucleating a zinc gallate spinel structure with fermentative or thermophilic bacteria, in accordance with the present disclosure.

The above-described process may also be performed in a continuous arrangement as shown schematically by the bioreactor 40 shown in FIG. 3. The bioreactor 40 operates in a similar manner as the bioreactor 30 of FIG. 2. The bioreactor 40 includes a fluid recirculator 41 that allows the culture medium 32 to pass through an external trap 42 from which the precipitated divalent metal gallate spinel 36 can be removed. The trap 42 may separate the precipitated divalent metal gallate spinel 36 from the circulating culture medium by settling, due to the greater density of the divalent metal gallate spinel 36. In some cases, the collection process of the precipitated divalent metal gallate spinel 36 can be assisted by using a continuous centrifuge 43. Continuous collection of product from the circulating fluid may also be used as a means of controlling particle size, because the particles tend to grow larger the longer they remain in the culture. An additional fluid valve 44 may be provided through which additional culture medium or nutrients 34 may be added from an external reservoir 45 while maintaining the anaerobic conditions within the container 32.

The divalent metal gallate spinel structures foamed using the process flow depicted in FIG. 1A, and the apparatuses depicted in FIGS. 2 and 3, may be an undoped or pure divalent metal gallate spinel structure. By "pure" is meant that the spinel structure is completely free of dopants, such as manganese (Mn), cobalt (Co), chromium (Cr), europium (Eu), dysprosium (Dy) and combinations thereof. Alternatively, the spinel structure may be doped by one or more metals, such as any of the foregoing exemplary metals. The only elements present in a pure zinc gallate spinel structure are those within the formulation $A^{2+}B_2^{3+}O_4^{2-}$, in which cations A and B occupy some or all of the tetrahedral and octahedral sites in the lattice, wherein 98% of the A site is occupied by a divalent metal cation and 98% of the B site is occupied by a gallium cation. In some embodiments, impurities may be present so long as their concentration does not change the emission for the wavelength of the divalent metal gallate spinel structures. For example, the impurities may be elements that are not within the desired stoichiometry for the A site and the B site of the formulation $A^{2+}B_2^{3+}O_4^{2-}$, which may result from the processing. Some examples of impurity include, but are not limited to phosphorus, silicon, carbon and aluminum. In one example, a pure divalent metal gallate spinel structure has the formulation $A^{2+}B_2^{3+}O_4^{2-}$, in which cations A and B occupy some or all of the tetrahedral and octahedral sites in the lattice, wherein about 100% of the A site is occupied by a divalent metal cation and about 100% of the B site is occupied by a gallium cation.

In some embodiments, the undoped divalent metal (and particularly, zinc) gallate spinel structure may function as a blue and/or violet light emitting phosphor. In one embodiment, the wavelength of the undoped divalent metal gallate spinel may exhibit a peak ranging from 400 nm to 495 nm. In another embodiment, the wavelength of the undoped divalent metal gallate spinel ranges from 425 nm to 435 nm. In some examples, the peak wavelength of light emission of the undoped divalent metal gallate spinel is 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, and 490 nm, or may be within a range bounded by any of these values.

Figure 4:
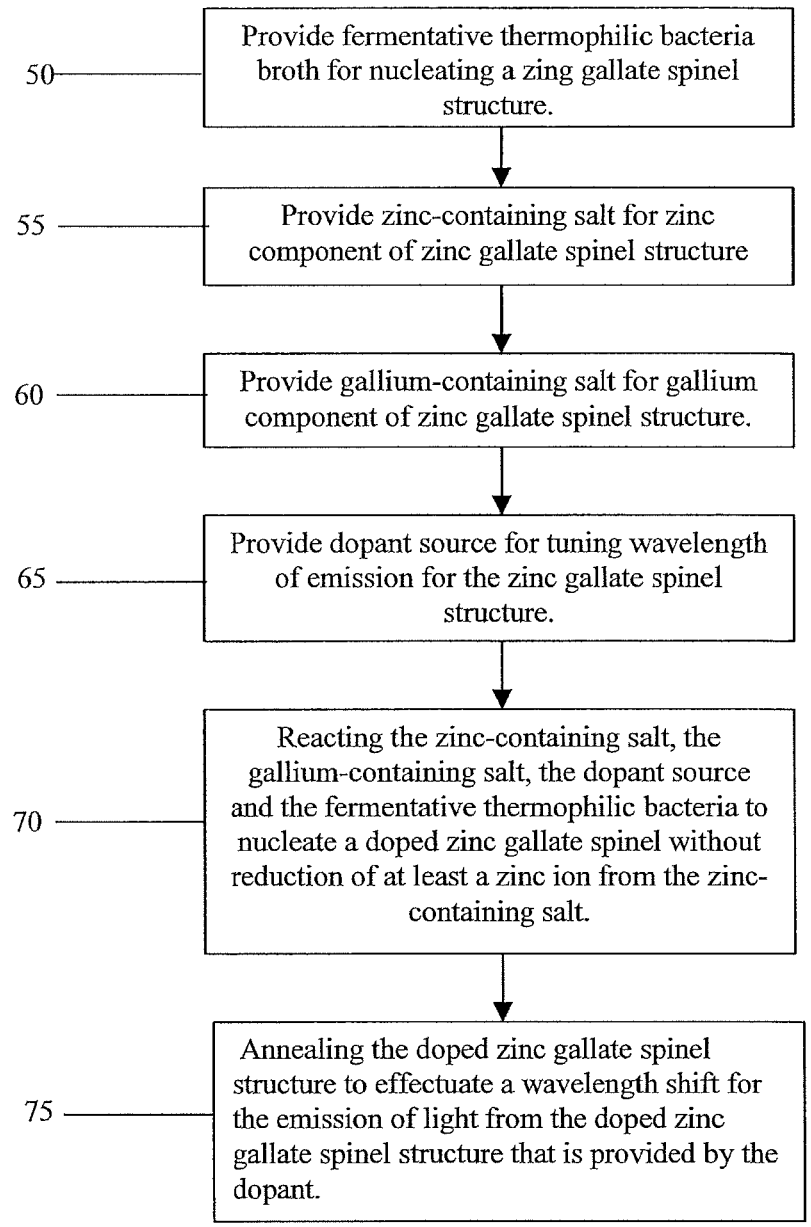
FIG. 4 is a process diagram illustrating a method of forming doped zinc gallate spinel structures with fermentative or thermophilic bacteria, in accordance with one embodiment of the present disclosure.

FIG. 4 is a process diagram illustrating a method of forming doped divalent metal gallate spinel structures with fermentative or thermophilic bacteria. The process flow depicted in FIG. 4 is similar to the process flow that is described above with reference to FIG. 1A with the exception that a dopant source is combined with the divalent metal-containing salt, the gallium-containing salt, and the fermentative or thermophilic bacteria. The fermentative or thermophilic bacteria, divalent metal-containing salt and gallium-containing salt that are described above in the process sequence depicted in FIG. 1A are suitable for the fermentative or thermophilic bacteria, divalent metal-containing salt and gallium-containing salt of the method of forming a doped divalent metal gallate spinel structure as illustrated in FIG. 4. Therefore, the description of steps 5, 10 and 15 of the method of nucleating a divalent metal gallate spinel structure with fermentative or thermophilic bacteria that is described with reference to FIG. 1A, is suitable for the description of steps 50, 55 and 60 of the method of forming doped divalent metal gallate spinel structures with fermentative or thermophilic bacteria that is illustrated in FIG. 4.

Referring to step 65 of FIG. 4, in one embodiment, a dopant source is provided for tuning a wavelength of emission from the divalent metal gallium spinel structure, wherein the dopant source may be selected from the group consisting of manganese (Mn), chromium (Cr), europium (Eu), dysprosium (Dy), cobalt (Co), and combinations thereof. The dopant may be any element of the Periodic Table. In some embodiments, one or more dopants are excluded. Typically, the dopants are substitution type dopants. A substitution type dopant replaces a portion of the elements that occupy the A and B lattice sites for the divalent metal gallate spinel structure, which has the spinel formulation $A^{2+}B_2^{3+}O_4^{2-}$. For example, in one embodiment, in which the dopant is manganese (Mn) having an oxidation state of 2+, the manganese ion ($Mn^{2+}$) may be substituted for the divalent metal ion (e.g., $Zn^{2+}$) that occupies the A lattice site of the spinel having the formulation $A^{2+}B_2^{3+}O_4^{2-}$. In the embodiments in which the dopant is manganese (Mn) having the oxidation state 3+, the manganese ion ($Mn^{3+}$) may be substituted for the gallium ion ($Ga^{3+}$) that occupies the B lattice site of the spinel having the formulation $A^{2+}B_2^{3+}O_4^{2-}$. The occupancy to either tetrahedral or octahedral site may vary according to doping elements, concentration, valences, ionic radii, therefore divalent dopants may occupy octahedral sites in some extent or trivalent dopants may occupy tetrahedral sites in some extent.

In one embodiment, to dope the divalent metal gallate spinel structure with a manganese (Mn) dopant, i.e., $Mn^{2+}$ or $Mn^{3+}$, at least one of manganese chloride hydrate ($MnCl_2 \cdot xH_2O$), manganese nitrate hydrate ($Mn(NO_3)_2 \cdot xH_2O$), manganese sulfate hydrate ($MnSO_4 \cdot xH_2O$), manganese iodide ($MnI_2$), manganese bromide ($MnBr_2$), manganese fluoride ($MnF_3$), manganese acetate hydrate (Mn ($CH_3COO)_2.xH_2O$), and manganese carbonate ($MnCO_3$), is mixed with the aqueous solution including the divalent metal-containing salt, the gallium-containing salt and the fermentative or thermophilic bacteria. according to the process described earlier above to produce a divalent metal gallate spinel structure doped with manganese. The concentration of manganese (Mn) dopant, i.e., $Mn^{2+}$ or $Mn^{3+}$, may range from 0.01% to 10% of divalent metal, gallium, or their combined concentration. In another embodiment, the concentration of manganese (Mn) dopant, i.e., $Mn^{2+}$ or $Mn^{3+}$, may range from 0.02% to 8%. In yet another embodiment, the concentration of manganese (Mn) dopant, i.e., $Mn^{2+}$ or $Mn^{3+}$, ranges from 0.04% to 6%. In some examples, the concentration of manganese (Mn) dopant, i.e., $Mn^{2+}$ or $Mn^{3+}$, may be 0.01%, 2%, 4%, 6%, and 8%. Any range of manganese (Mn) concentration between the aforementioned examples is also contemplated. The doping of the divalent metal gallate spinel with manganese (Mn) dopant, i.e., $Mn^{2+}$ or $Mn^3$, when treated with the subsequently described heat treatment provides a wavelength of light emission that ranges from 495 nm to 570 nm.

In one embodiment, to dope the divalent metal gallate spinel structure with a chromium dopant, e.g., $Cr^{3+}$, at least one of chromium chloride hydrate ($CrCl_3.xH_2O$), chromium nitrate hydrate ($Cr(NO_3)_3.xH_2O$), chromium acetate hydroxide (($CH_3CO_2)_7Cr_3(OH)_2$), chromium sulfate hydrate ($Cr_2(SO_4)_3.xH_2O$), chromium fluoride hydrate ($GaF_3.xH_2O$), chromium iodide hydrate ($CrI_3.xH_2O$), chromium bromide hydrate ($CrBr_3.xH_2O$), and chromium phosphate hydrate ($Cr(PO_4).xH_2O$) is mixed with the aqueous solution including the divalent metal-containing salt, the gallium-containing salt and the fermentative or thermophilic bacteria according to the process described earlier above the produce a divalent metal gallate spinel structure doped with chromium. The chromium dopant, i.e., $Cr^{3+}$, is a substitutional dopant for gallium, in the divalent metal gallate spinel structure. More specifically, the chromium dopant, i.e., $Cr^{3+}$, occupies the B lattice site of the spinel having the formulation $A^{2+}B_2^{3+}O_4^{2-}$. The concentration of chromium (Cr) dopant, i.e., $Cr^{3+}$, may range from 0.01% to 6% of divalent metal, gallium, or their combined concentration. In another embodiment, the concentration of chromium (Cr) dopant, i.e., $Cr^{3+}$, may range from 0.04% to 6%. In yet another embodiment, the concentration of chromium (Cr) dopant, i.e., $Cr^{3+}$, ranges from 0.08% to 4%. In some examples, the concentration of chromium (Cr) dopant, i.e., $Cr^{3+}$, may be 0.01%, 0.5%, 2%, 4% or 6%. Any range of chromium (Cr) concentration between the aforementioned examples is also contemplated. The doping of the zinc gallate spinel with chromium, e.g., $Cr^{3+}$, when treated with the subsequently described heat treatment provides a wavelength of light emission that ranges from 570 nm to 750 nm.

In one embodiment, to dope the divalent metal gallate spinel structure with a europium dopant, e.g., $Eu^{3+}$, at least one of europium chloride hydrate ($EuCl_3.xH_2O$), europium fluoride hydrate ($EuF_3.xH_2O$), europium nitrate hydrate ($Eu(NO_3)_3.xH_2O$), europium acetate hydroxide (($CH_3CO_2)_7Eu_3(OH)_2$), europium bromide hydrate ($EuBr_3.xH_2O$) and europium sulfate hydrate ($Eu_2(SO_4)_3.xH_2O$) is mixed with the aqueous solution including the divalent metal-containing salt, the gallium-containing salt and the fermentative or thermophilie bacteria according to the process described earlier above to produce a divalent metal gallate spinel structure doped with europium. The europium dopant, i.e., $Eu^{3+}$, is a substitutional dopant for gallium, in the divalent metal gallate spinel structure. More specifically, the europium dopant, i.e., $Eu^{3+}$, occupies the B lattice site of the spinel having the formulation $A^{2+}B_2^{3+}O_4^{2-}$. The concentration of europium (Eu) dopant, i.e., $Eu^{3+}$, may range from 0.01% to 20% of divalent metal, gallium, or their combined concentration. In another embodiment, the concentration of europium (Eu) dopant, i.e., $Eu^{3+}$, may range from 0.01% 20% of divalent metal, gallium, or their combined concentration. In yet another embodiment, the concentration of europium (Eu) dopant, i.e., $Eu^{3+}$, ranges from 0.04% to 15%. In some examples, the concentration of europium (Eu) dopant, i.e., $Eu^{3+}$, may be 0.01%, 0.5%, 2%, 5%, 10% and 20%. Any range of europium (Eu) concentration between the aforementioned examples is also contemplated. The doping of the zinc gallate spinel with europium (Eu) dopant e.g. $Eu^{3+}$, when treated with the subsequently described heat treatment provides a wavelength of light emission that ranges from 570 nm to 750 nm.

In one embodiment, to dope the divalent metal gallate spinel structure with a dysprosium (Dy) dopant, e.g., $Dy^{3+}$, at least one of dysprosium chloride hydrate ($DyCl_3.xH_2O$), dysprosium fluoride hydrate ($DyF_3.xH_2O$), dysprosium nitrate hydrate ($Dy(NO_3)_3.xH_2O$), dysprosium acetate hydroxide (($CH_3CO_2)_7Dy_3(OH)_2$), dysprosium bromide hydrate ($DyBr_3.xH_2O$), and dysprosium sulfate hydrate ($Dy_2(SO_4)_3.xH_2O$) is mixed with the aqueous solution including the divalent metal-containing salt, the gallium-containing salt and the fermentative or thermophilic bacteria according to the process described earlier above to produce a divalent metal gallate spinel structure doped with dysprosium. The dysprosium dopant, i.e., $Dy^{3+}$, is a substitutional dopant for gallium, in the divalent metal gallate spinel structure. More specifically, the dysprosium dopant, i.e., $Dy^{3+}$, occupies the B lattice site of the spinel having the formulation $A^{2+}B_2^{3+}O_4^{2-}$. The concentration of dysprosium (Dy) dopant, i.e., $Dy^{3+}$, may range from 0.01% to 10% of divalent metal, gallium, or their combined concentration. In another embodiment, the concentration of dysprosium (Dy) dopant, i.e., $Dy^{3+}$, may range from 0.02% to 8%. In yet another embodiment, the concentration of dysprosium (Dy) dopant, i.e., $Dy^{3+}$, ranges from 0.04% to 6%. In some examples, the concentration of dysprosium (Dy) dopant, i.e., $Dy^{3+}$, may be 0.01%, 0.5%, 2%, 4%, and 7%. Any range of dysprosium (Dy) concentration between the aforementioned examples is also contemplated. The doping of the zinc gallate spinel with dysprosium (Dy) dopant, e.g. $Dy^{3+}$, when treated with the subsequently described heat treatment provides a wavelength of light emission that ranges from 450 nm to 510 nm. In another embodiment, the doping of the zinc gallate spinel with dysprosium (Dy) dopant, e.g. $Dy^{3+}$, when treated with the subsequently described heat treatment provides a wavelength of light emission that ranges from 560 nm to 610 nm. In an even further embodiment, the doping of the zinc gallate spinel with dysprosium (Dy) dopant, e.g. $Dy^{3+}$, when treated with the subsequently described heat treatment provides a wavelength of light emission that ranges from 755 nm to 810 nm. In some embodiments, zinc gallate spinel structure with a dysprosium (Dy) dopant can produce white light by itself. In some examples, zinc gallate spinel structures doped with a dysprosium (Dy) has 4 groups of characteristic lines in the dopant emission spectra at the same time, e.g., lines in blue region (450 nm to 510 nm), lines in the yellow region (560 nm-610 nm), and two groups of line spectra in the red region 660 nm to 720 nm and 755 nm to 800 nm).

In one embodiment, to dope the divalent metal gallate spinel structure with a cobalt dopant, e.g., $Co^{2+}$, at least one of cobalt chloride hydrate ($CoCl_2.xH_2O$), cobalt nitrate hydrate ($Co(NO_3)_2.xH_2O$), cobalt sulfate hydrate ($CoSO_4 \cdot xH_2O$), cobalt iodide ($CoI_2$), cobalt bromide ($CoBr_2$), cobalt fluoride ($CoF_3$), cobalt acetate hydrate ($Co(CH_3COO)_2 \cdot xH_2O$), and cobalt carbonate ($CoCO_3$), is mixed with the aqueous solution including the divalent metal-containing salt, the gallium-containing salt, and the fermentative or thermophilic bacteria according to the process described earlier above to produce a divalent metal gallate spinel structure doped with cobalt. The cobalt dopant, i.e., $Co^{2+}$, is a substitutional dopant for the divalent metal in the divalent metal gallate spinel structure. More specifically, the cobalt dopant, i.e., $Co^{2+}$, occupies the A lattice site of the spinel having the formulation $A^{2+}B_2^{3+}O_4^{2-}$. The dopant source for the cobalt dopant is mixed with the aqueous solution including the divalent metal-containing salt, the gallium-containing salt, and the fermentative or thermophilic bacteria. The concentration of cobalt (Co) dopant, i.e., $Co^{2+}$, may range from 0.01% to 10% of divalent metal, gallium, or their combined concentration. In another embodiment, the concentration of cobalt (Co) dopant, i.e., $Co^{2+}$, may range from 0.02% to 8%. In yet another embodiment, the concentration of cobalt (Co) dopant, i.e., $Co^{2+}$, ranges from 0.04% to 6%. In some examples, the concentration of cobalt (Co) dopant, i.e., $Co^{2+}$, may be 0.02%, 0.5%, 2%, 4%, and 10%. Any range of cobalt (Co) concentration between the aforementioned examples is also contemplated. The doping of the zinc gallate spinel with cobalt (Co) dopant, e.g. $Co^{2+}$, when treated with the subsequently described heat treatment provides a wavelength of light emission of blue and visible and near infrared emission that ranges from 400 nm to 495 nm with the maximum peak of 470 nm using the excitation at 254 nm.

Referring to step 70 of FIG. 4, in one embodiment, the divalent metal-containing salt, the gallium-containing salt, the doping source, e.g., at least one of manganese (Mn), chromium (Cr), europium (Eu), dysprosium (Dy), and cobalt (Co), and the bacteria are combined to nucleate a doped divalent metal gallate spinel structure. Typically, the nucleation of the doped divalent metal gallate spinel structure does not include a reduction reaction. Step 70 of combining the reactants for the process flow that is described with reference to FIG. 4 is similar to step 20 of combining the reactants for the process flow that is described with reference to FIG. 1A with the exception that the process flow depicted in FIG. 4 further includes a dopant source for the divalent metal gallate spinel structure. Therefore, the description of step 20 in FIG. 1A for reacting the divalent metal-containing salt, the gallium-containing salt, and the fermentative or thermophilic bacteria to nucleate a divalent metal gallate spinel without a reduction reaction is suitable for the description of reacting the divalent metal-containing salt, the gallium-containing salt, the dopant source, and the fermentative or thermophilic bacteria in step 70 of the process flow for forming a doped divalent metal gallate spinel structure that is depicted in FIG. 4. Further, the above described batch reactor that is depicted in FIG. 2, and the continuous reactor that is described with reference to FIG. 3, may each be employed at step 70 for reacting the divalent metal-containing salt, the gallium-containing salt, the dopant source, and the fermentative or thermophilic bacteria in step 70 of the process flow for forming a doped divalent metal gallate spinel structure that is illustrated in FIG. 4.

Referring to step 75 of FIG. 4, in one embodiment, the doped divalent metal gallate spinel structures are typically annealed to effectuate a wavelength shift from the dopant that has been introduced to the spinel structure. The annealing process can provide phosphors having emissions at green, yellow, orange or red wavelengths. For example, the annealing process may effectuate a wavelength shift (from pure divalent metal gallate to the doped version) from approximately 450 nm to another peak position. In some embodiments, the annealing process is applied to zinc gallate structures that are doped with manganese (Mn), chromium (Cr), europium (Eu), cobalt (Co), dysprosium (Dy) and combinations thereof.

The annealing process may be provided by a thermal annealing process, such as rapid thermal annealing, furnace annealing, laser annealing, induction heating, or pulsed thermal processing, all of which are well known in the art. The annealing atmosphere may be an inert atmosphere, such as an argon (Ar) or nitrogen ($N_2$) atmosphere. In other embodiments, the annealing atmosphere may be an oxygen-containing atmosphere, such as air. In one embodiment, the doped divalent metal gallate spinel is annealed at a temperature ranging from 750° C. to 1050° C. In another embodiment, the doped divalent metal gallate spinel may be annealed at a temperature ranging from 800° C. to 1000° C. In yet another embodiment, the doped divalent metal gallate spinel may be annealed at a temperature ranging from 850° C. to 950° C. It is noted that the annealing can be in a range bounded by any values between any of the endpoints of the above ranges. In particular embodiments, the doped divalent metal gallate spinel may be annealed at 810° C., 825° C., 850° C., 875° C., 900° C., 925° C., 950° C., 975° C. or within a range bounded by any two of the foregoing values. The time for annealing may be as great as two hours. In some embodiments, the time for annealing the doped divalent metal gallate spinel structures may range from 15 minutes to 45 minutes. In other embodiments, the time for annealing the doped divalent metal gallate spinel structure may range from 20 to 40 minutes.

In particular embodiments, a pulse thermal process is used in the annealing step. The pulse thermal method considered herein can be any method that can subject particles to a pulse of intense thermal (i.e., radiant) energy. Generally, the means by which the radiant energy is produced does not substantially alter or degrade the composition of the particles. In particular embodiments, the radiant pulse is provided by an intense pulse of electromagnetic radiation. To produce heat in a material, the electromagnetic radiation is generally absorbed by the material and emitted as thermal energy.

The annealing step can employ any temperature sufficient to induce a wavelength shift. The temperature of the thermal pulse can widely vary depending on the composition of the particles and the type of particles desired (e.g., crystalline vs. amorphous). In different embodiments, the thermal pulse employs a temperature of precisely, about, at least, above, up to, or less than, for example, 50, 75, 100, 120, 125, 150, 200, 250, 300, 350, 400, 450, 500, 600, 700, 800, 900, 1000, 1500, 1800, 2000, 2200, 2500, or 3000 degrees Celsius (° C.), or a temperature within a range bounded by any two of the foregoing exemplary temperature values, wherein the term "about", used for the temperature, generally indicates within ±5, ±4, ±3, ±2, or ±1° C. of the indicated temperature.

In the pulsed thermal process, one or more pulses are applied to the particles. In one embodiment, a single pulse is used. In another embodiment, more than one pulse (e.g., two, three, or a multiplicity of pulses), separated by a time interval between pulses, is used. The pulse duration of each pulse can widely vary depending on such factors as the absorbing ability of the particles, the particle size, the wavelength of light, the temperature, and substrate (underlying layers) used. It is understood that a longer pulse duration generally results in a higher applied temperature.

Generally, the pulse duration is no more than 10, 5, or 1 second, and more typically, 100-500 milliseconds (ms). In different embodiments, the pulse duration can be precisely, about, at least, up to, or less than, for example, 1 second (i.e., 1000 ms), 500 ms, 400 ms, 300 ms, 200 ms, 100 ms, 50 ms, 20 ms, 10 ms, 5 ms, 1 ms (i.e., 1000 microseconds, i.e., 1000 µs), 900 µs, 800 µs, 700 µs, 600 µs, 500 µs, 400 µs, 300 µs, 200 µs, 100 µs, 80 µs, 50 µs, 40 µs, 30 µs, 20 µs, 10 µs, 5 µs, 2.5 µs, 1 µs, 0.5 µs, 0.25 µs, or 0.1 µs, or a pulse duration within a range bounded by any of the foregoing exemplary values. In different embodiments, the pulse energy can be, precisely, about, at least, up to, or less than, for example, 1, 2, 5, 10, 25, 50, 100, 200, 300, 400, 500, 600, 700, 800, 900, or 1000 J/cm$^2$. As known in the art, a pulse power (i.e., in W/cm$^2$) can be derived by dividing the pulse energy (i.e., in J/cm$^2$) by the pulse duration (in seconds). In the particular case of thermally treating particles on thermally sensitive substrates (e.g., a plastic), the pulse thermal process preferably employs a high energy density (e.g., >20 KW/cm$^2$) thermal pulse at low ambient temperature.

If multiple pulses are used, the pulse duration may be the same or the pulse duration may vary across different pulses. For example, in different embodiments, the pulse duration alternates, or successively increases or decreases with time. When multiple pulses are used, the time interval between pulses (i.e., the periodicity) can also be appropriately selected. In different embodiments, the time interval is maintained below the pulse duration, maintained above the pulse duration, or increased or decreased with time successively or in a pattern-wise manner. The time interval can be, for example, precisely, about, at least, up to, or less than, for example, any of the exemplary values provided above for pulse duration, typically no more than about 1 or 2 seconds. The time interval may also be within a range bounded by any of the aforesaid values and/or any of the values provided above for pulse duration. The frequency of the pulses can be precisely, about, at least, up to, or less than, for example, 1 min$^{-1}$, 10 min$^{-1}$, 20 min$^{-1}$, 30 min$^{-1}$, 40 min$^{-1}$, 50 min$^{-1}$, 1 sec$^{-1}$ (1 Hz), 5 sec$^{-1}$, 10 sec$^{-1}$, 20 sec$^{-1}$, 30 sec$^{-1}$, 40 sec$^{-1}$, 50 sec$^{-1}$, 100 sec$^{-1}$, 500 sec$^{-1}$, 1000 sec$^{-1}$, 5000 sec$^{-1}$, $1\times10^4$ sec$^{-1}$, $5\times10^4$ sec$^{-1}$, $1\times10^5$ sec$^{-1}$, $5\times10^5$ sec$^{-1}$, $1\times10^6$ sec$^{-1}$, $5\times10^6$ sec$^{-1}$, $1\times10^7$ sec$^{-1}$, or $5\times10^7$ sec$^{-1}$, or a frequency within a range bounded by any of the foregoing exemplary values.

The pulse of electromagnetic radiation may be suitably adjusted in several other ways. For example, the pulse of electromagnetic radiation can be suitably adjusted, by means well known in the art, in its amplitude, phase, and extent of collimation. Collimation can be achieved by, for example, use of a collimator, such as a collimation lens or parabolic or spherical mirrors. Substantially collimated light corresponds to a laser emission, which is also considered herein as the pulse of electromagnetic radiation. The spectrum of the impinging radiation may also be appropriately filtered to provide particular wavelengths or a narrowed range of wavelengths.

The pulse of electromagnetic radiation can also be suitably adjusted in its power (i.e. intensity). The intensity of the pulse of electromagnetic radiation is generally at least 100 W/cm$^2$. In different embodiments, the pulse of electromagnetic radiation can be precisely, about, at least, or above, for example, 100, 200, 500, 1000, 2000, 3000, 4000, 5000, 6000, 7000, 8000, 9000, $1\times10^4$, $1.5\times10^4$, $2\times10^4$, $2.5\times10^4$, $3\times10^4$, $3.5\times10^4$, $4\times10^4$, $4.5\times10^4$, $5\times10^4$, $5.5\times10^4$, $6\times10^4$, $6.5\times10^4$, $7\times10^4$, $7.5\times10^4$, $8\times10^4$, $9\times10^4$, or $1\times10^5$ W/cm$^2$, or an intensity within a range bounded by any of the foregoing exemplary values.

In particular embodiments, the pulsed thermal method employs a stabilized plasma arc high intensity radiation source, as described, for example, in U.S. Pat. Nos. 4,027,185 and 4,700,102, the contents of which are incorporated herein by reference in their entirety. As described in said patents, the arc can be suitably restricted by use of a vortexing liquid wall. Numerous modifications and improvements of the plasma arc method are known. For example, the instant invention incorporates by reference the contents of U.S. Pat. No. 4,937,490, which describes a high intensity radiation arc apparatus that includes liquid injecting means, gas injecting means, and exhausting means in the arc chamber in order to provide a liquid vortex motion and a gas vortex motion to restrict the plasma arc. Further adjustments, modifications, and optimizations of the processes and apparatuses taught in the foregoing patents can be made to better conform with the aims and goals of the instant invention, as described above. For example, the processes and apparatuses taught in the foregoing patents can be configured to emit a high intensity of electromagnetic radiation, particularly of the infrared wavelengths. Other modifications not contemplated in said foregoing patents may also be necessary to make the arc plasma systems described therein capable of operating within the parameters described herein, e.g., to provide any of the particular pulse durations, frequencies, power, or wavelengths described above. In particular embodiments, the thermal pulse method described herein utilizes a plasma arc lamp with an argon plasma. The use of a plasma arc lamp with an argon plasma provides the particular advantage of providing a significantly increased operating space compared to other thermal pulse configurations of the art, such as those using a flash lamp, particularly a xenon flash lamp.

As indicated above, the divalent metal gallate spinel structure may be employed as a phosphor. A phosphor is any material that, when exposed to radiation, emits visible light. The impinging radiation may be, for example, ultraviolet light (e.g., 254 nm to 288 nm) or a beam of electrons. In one application of the above-described divalent metal gallate spinel structures, divalent metal gallate spinel structures including doped divalent metal gallate spinel structures that emit wavelengths of light within the red, green, and blue spectra are mixed to provide white light suitable for efficient solid state lighting. White light is a mixture of the colors of the visible spectrum. This "visible light" corresponds to a wavelength range of 400 nm to 700 nm, and a color range of violet through red.

In one embodiment, a method of forming a structure for emitting white light is provided by forming a first phosphor of a first doped zinc gallate spinel structure that is nucleated by a fermentation with a thermophilic bacteria and annealing, wherein the first phosphor emits a first wavelength of red light ranging from 570 nm to 750 nm. This first phosphor may be formed in accordance with steps 50-75 of FIG. 4, in which zinc gallate spinel structure is doped with chromium (Cr), e.g., chromium (Cr$^{3+}$), or europium (Eu), e.g., europium (Eu$^{3+}$). The concentration of the chromium (Cr) dopant and the chromium (Cr$^+$) dopant source has been provided above with reference to step 65 of FIG. 4. The concentration of the europium (Eu) dopant, and the europium (Eu$^{3+}$) dopant source have been described above with reference to FIG. 4. The annealing conditions applied to the zinc gallate spinel structures doped with chromium (Cr) and/or europium (Eu) dopant have been described above with reference to step 75 of FIG. 4.

In one embodiment, a second phosphor may be formed to mix with at least the first phosphor in order to provide white light. The second phosphor may be a second doped zinc gallate spinel structure that is nucleated by a second fermentation with thermophilic bacteria and annealing in accordance with steps 50-75 of FIG. 4. The second phosphor may be doped to emit a wavelength of green light ranging from 495 nm to 570 nm. The zinc gallate spinel structure that provides the second phosphor may be doped with a manganese (Mn) dopant, e.g., $Mn^{2+}$. The concentration of the manganese (Mn) dopant and the manganese ($Mn^{2+}$) dopant source have been described above with reference to step 65 of FIG. 4. The annealing conditions applied to the zinc gallate spinel structures doped with manganese (Mn) dopant have been described above with reference to step 75 of FIG. 4.

In one embodiment, a third phosphor may be formed to mix with at least one of the first and second phosphor in order to provide white light. The third phosphor may be a zinc gallate spinel structure that is nucleated by a fermentation with thermophilic bacteria in accordance with steps 5-20 of FIG. 1A. The third phosphor may emit a wavelength of blue light ranging from 400 nm to 495 nm. In some embodiments, the wavelength of light being emitted from the phosphor that provides the emission of blue light may be the similar or shifted to a higher wavelength than the undoped zinc gallate spinel structure by introducing a cobalt dopant and annealing the zinc gallate spinel structure that has been doped with cobalt. The concentration of the cobalt (Co) dopant and the cobalt ($Co^{2+}$) dopant source have been described above with reference to step 65 of FIG. 4. The zinc gallate spinel structure that has been doped with cobalt (Co) is typically annealed to provide a wavelength shift within a range of wavelengths ranging from 400 nm to 495 nm with the maximum peak of 470 nm using the excitation at 254 nm. The annealing conditions applied to the zinc gallate spinel structures doped with cobalt (Co) have been described above with reference to step 75 of FIG. 4. In some embodiments, the cobalt dopant that has been added to the doped zinc gallate spinel structure increases the intensity of the emission of blue light of the zinc gallate spinel structure. For example, a cobalt doped zinc gallate spinel structure may exhibit an emission of blue light having an increase in intensity ranging from 180% to 240% when compared to the intensity of emitted blue light from an undoped zinc gallate spinel structure without annealing in FIG. 9.

In some embodiments, a fourth phosphor may also be mixed with at least one of the first phosphor, the second phosphor and the third phosphor in order to provide a white light producing structure. In some embodiments, the fourth phosphor may be used without mixing with any first, second, or third phosphor to provide a white light producing structure. In some embodiments, the fourth phosphor may be a zinc gallate spinel structure that is doped with dysprosium (Dy), e.g., $Dy^{3+}$. The wavelength of light emission for the dysprosium (Dy) doped zinc gallate spinel may range from 450 nm to 510 nm, 560 nm to 610 nm, 660 nm to 720 nm or 755 nm to 810 nm. The concentration of the dysprosium (Dy) dopant source have been described above with reference to step 65 of FIG. 4. The zinc gallate spinel structure that has been doped with dysprosium (Dy) is typically annealed either to provide a wavelength shift within a range of wavelengths ranging within ±5 nm, ±10 nm, ±15 nm, ±20 nm, ±25 nm, ±30 nm, ±40 nm, ±50 nm or any range resulting from any two of the foregoing values from the 450 nm to 510 nm, 560 nm to 610 nm, 660 nm to 720 nm or 755 nm to 810 nm or to provide increased emission. The annealing conditions applied to the zinc gallate spinel structures doped with dysprosium (Dy) have been described above with reference to step 75 of FIG. 4.

The selected combination including at least two of the first phosphors, the second phosphor, the third phosphor and the fourth phosphor may be mechanically mixed to provide a mixture in which the amounts of the selected first, second, third and fourth phosphor are selected so that the combination of the emitted wavelengths from the phosphor mixture provides a white light. The percentage by weight for each of the divalent metal gallate spinel structures in the mixture of the at least two of the first, second, third and fourth phosphor may be a range that is selected from the group of 1% to 100%, 10% to 90%, 20% to 80%, 30% to 70%, 40% to 60% and 50%. In one embodiment, white light emission can be provided by a mixture of 50-80% of the first phosphor of red, 15-35% of the second phosphor of green, and 5-15% of the third phosphor of blue produce white emission. The mixture may be a homogeneous distribution of each of the divalent metal gallate spinel structures that provide the phosphors. Mixing of the at least two of the first phosphors, the second phosphor, the third phosphor, and the fourth phosphor may be provided using mechanical means, such as stirring. The mixture may be fabricated into a design in a heterogeneous manner laterally or horizontally to provide a three-dimensional distribution for a specific device application.

Figure 5:
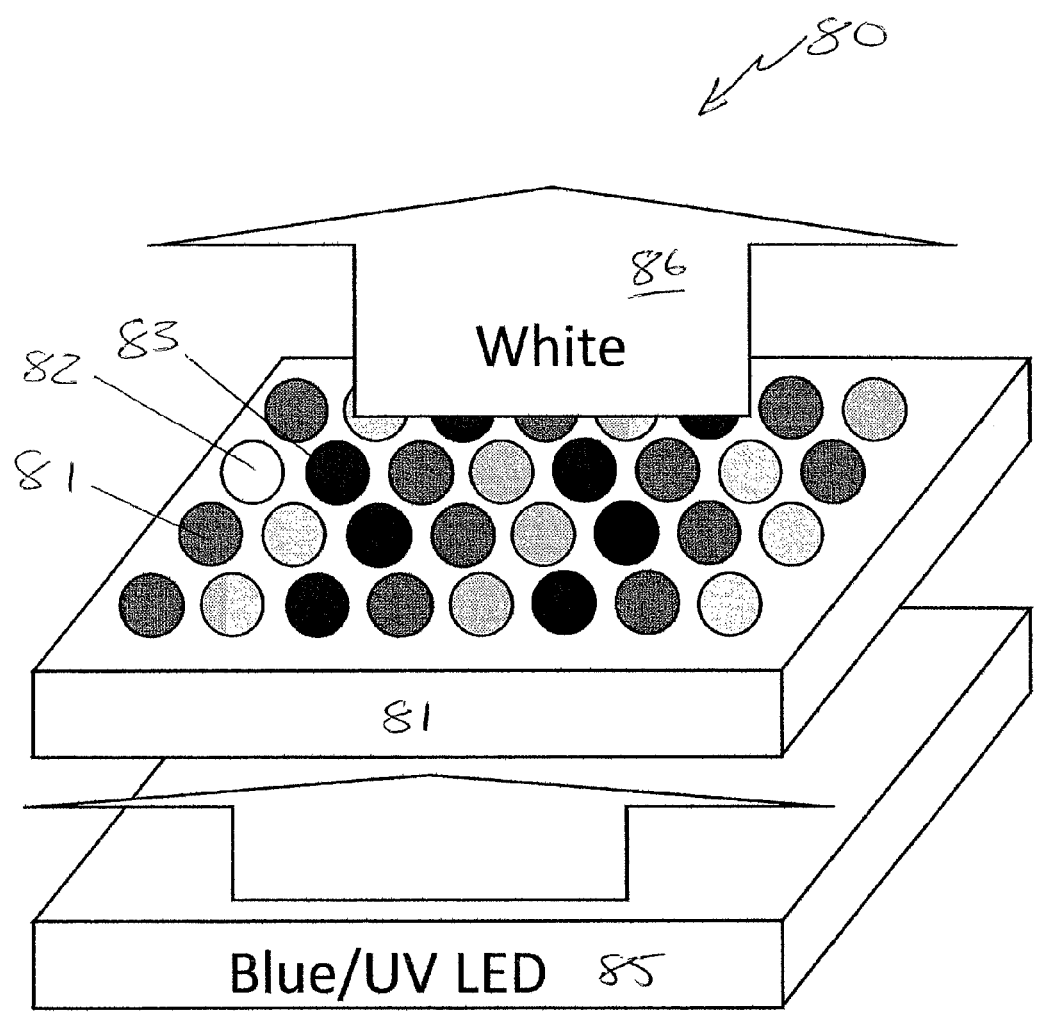
FIG. 5 is a perspective view of a structure for emitting white light from doped phosphors produced by fermentation of zinc-containing salts and gallium-containing salts with thermophilic bacteria and tuned by dopants, in accordance with one embodiment of the present disclosure.

Although the white light-emitting structure may be a mixture of divalent metal gallate spinel structures that provides at least two phosphors that emit different wavelengths of light in a mixed powder form, embodiments are contemplated in which the white light-emitting structure further includes the mixture of the divalent metal gallate spinel structures in a binder, as depicted in FIG. 5. FIG. 5 depicts an embodiment of a white light-emitting structure 80 composed of phosphors of zinc gallate spinel structures and doped zinc gallate spinel structures that are formed in accordance with the methods described above with reference to FIGS. 1 and 4.

Referring to FIG. 5, in some examples, the zinc gallate spinel structures may be incorporated within a transparent substrate 81 by mixing a binder with the zinc gallate spinel structures, wherein the binder provides a matrix of the transparent substrate 81 and the doped zinc gallate spinel structures provides a dispersed phase within the transparent substrate 81. The zinc gallate spinel structures that are contained within the transparent substrate 81 may include a first zinc gallate spinel structure 82 that is doped with chromium (Cr) or europium (Eu) to provide a red light emitting phosphor, a second zinc gallate spinel structure 83 that is doped with manganese (Mn) provides a green light emitting phosphor, and a third zinc gallate spinel structure 84 that provides a blue light emitting phosphor. The foregoing example provided in FIG. 5 may also be generalized to any divalent metal gallate spinel structure.

In other embodiments, the doped zinc gallate spinel structures provides a dispersed phase within the transparent substrate 81. The zinc gallate spinel structures that are contained within the transparent substrate 81 may include one type of zinc gallate spinel structure 82 that is doped with dysprosium (Dy) to provide a white light. In other embodiments, single zinc gallate spinel structures that are contained within the transparent substrate 81 may include one type of zinc gallate structure 82 that is doped with mixed dopants of manganese (Mn), chromium (Cr), europium (Eu), cobalt (Co), dysprosium (Dy) and combinations thereof to provide a white light. The foregoing examples may also be generalized to any divalent metal gallate spinel structure.

Some methods of incorporating the divalent metal gallate spinel structure within a transparent substrate include cavity encapsulation and coating. In some embodiments, cavity encapsulation includes mixing the divalent metal gallate spinel structures that provide phosphors with a binder, such as epoxy or silicon. The mixture is then deposited on a supporting substrate, such as a glass substrate. In a coating process, the mixed powders of the divalent metal gallate spinel structures that provide the red, green, and blue light emitting phosphors are sprayed with a silicone/binder/solvent combination.

Referring to FIG. 5, in one embodiment, a blue light emitting diode/ultraviolet light emitting diode 85 is positioned to expose the transparent substrate 81 containing the phosphors provided by the zinc gallate spinel structures 82, 83, 84 to radiation. In response to the radiation exposure from the blue light emitting diode/ultraviolet light emitting diode 85, the first zinc gallate spinel structure 82 emits wavelengths of red light, the second zinc gallate spinel structure 83 emits wavelengths of green light and the third zinc gallate spinel structure 84 emits wavelengths of blue light, wherein the mixture of red, green and blue wavelengths provide white light 86. In some embodiments, a beam of electrons may be substituted for the blue light emitting diode/ultraviolet light emitting diode 85 to provide the radiation source that is applied to the zinc gallate spinel structures 82, 83, 84. In some embodiments, visible light may be substituted for the blue light emitting diode/ultraviolet light emitting diode 85 to provide the excitation source that is applied to the zinc gallate spinel structures 82, 83, 84 that can produce white light or specific color deviated from white light. Although, the structure depicted in FIG. 5 includes three different composition zinc gallate spinel structures 82, 83, 84, the present disclosure is not limited to only this embodiment, as any number of zinc gallate spinel structure compositions may be incorporated into the transparent substrate 81. Further, the selection of the composition of the wavelength of light does not have to be only white light. For example, the composition of the zinc gallate spinel structures that are contained within the transparent substrate may be selected to provide any visible wavelength of light emission, e.g., blue, cyan, green, yellow, orange, and red. Embodiments have also been contemplated in which the composition of the zinc gallate spinel structures is selected to emit ultraviolet and infrared wavelengths of light.

The following examples are provided to further illustrate the methods and structures of the present disclosure and demonstrate some advantages that arise therefrom. It is not intended that the present disclosure be limited to the specific examples described herein.

Zinc Gallate Spinel Structure Test Samples

Incubation of fermentative thermophilic bacteria was initiated in a medium that included 10 mM glucose and 2% (vol) mid-log growth *Thermoanaerobacter* sp. TOR-39 at 65° C. The pH was adjusted to be within the range of 6.5 to 8.5. After a period of 24 hours, precursor salts equivalent to 2 mM of target $ZnGa_2O_4$ were added, as specified in Table 1. More specifically, the fermentative thermophilic bacteria were incubated with metal ion precursor, i.e., zinc and gallium precursors, with doping elements, such as manganese (Mn), cobalt (Co), chromium (Cr), europium (Eu) and cobalt (Co), with consideration given to molar fraction as described in Table 1. The total precursor salt concentration was set to 6 mM.

TABLE 1

| Sample # | Target materials | Substituted element (%) | Precursor (salt) solution | | | | | | |
|---|---|---|---|---|---|---|---|---|---|
| | | | $Zn^{2+}$ (mM) | $Ga^{3+}$ (mM) | $Mn^{2+}$ (mM) | $Co^{2+}$ (mM) | $Cr^{3+}$ (mM) | $Eu^{3+}$ (mM) | $Dy^{3+}$ (mM) |
| 1 | $ZnGa_2O_4$ | | 2 | 4 | | | | | |
| 2 | $Zn_{0.99}Mn_{0.01}Ga_2O_4$ | Zn 1% | 1.98 | 4 | 0.02 | | | | |
| 3 | $Zn_{0.98}Mn_{0.02}Ga_2O_4$ | Zn 2% | 1.96 | 4 | 0.04 | | | | |
| 4 | $Zn_{0.96}Mn_{0.04}Ga_2O_4$ | Zn 4% | 1.92 | 4 | 0.08 | | | | |
| 5 | $Zn_{0.94}Mn_{0.06}Ga_2O_4$ | Zn 6% | 1.88 | 4 | 0.12 | | | | |
| 6 | $ZnGa_{1.98}Mn_{0.02}O_4$ | Ga 1% | 2 | 3.96 | 0.04 | | | | |
| 7 | $ZnGa_{1.96}Mn_{0.04}O_4$ | Ga 2% | 2 | 3.92 | 0.08 | | | | |
| 8 | $ZnGa_{1.92}Mn_{0.08}O_4$ | Ga 4% | 2 | 3.84 | 0.12 | | | | |
| 9 | $ZnGa_{1.88}Mn_{0.12}O_4$ | Ga 6% | 2 | 3.76 | 0.24 | | | | |
| 10 | $Zn_{0.99}Co_{0.01}Ga_2O_4$ | Zn 1% | 1.98 | 4 | | 0.02 | | | |
| 11 | $Zn_{0.98}Co_{0.02}Ga_2O_4$ | Zn 2% | 1.96 | 4 | | 0.04 | | | |
| 12 | $Zn_{0.96}Co_{0.04}Ga_2O_4$ | Zn 4% | 1.92 | 4 | | 0.08 | | | |
| 13 | $Zn_{0.94}Co_{0.06}Ga_2O_4$ | Zn 6% | 1.88 | 4 | | 0.12 | | | |
| 14 | $ZnGa_{1.98}Cr_{0.02}O_4$ | Ga 1% | 2 | 3.96 | | | 0.04 | | |
| 15 | $ZnGa_{1.96}Cr_{0.04}O_4$ | Ga 2% | 2 | 3.92 | | | 0.08 | | |
| 16 | $ZnGa_{1.92}Cr_{0.08}O_4$ | Ga 4% | 2 | 3.84 | | | 0.16 | | |
| 17 | $ZnGa_{1.88}Cr_{0.12}O_4$ | Ga 6% | 2 | 3.76 | | | 0.24 | | |
| 18 | $ZnGa_{1.80}Cr_{0.20}O_4$ | Ga 10% | 2 | 3.60 | | | 0.40 | | |
| 19 | $ZnGa_{1.98}Eu_{0.02}O_4$ | Ga 1% | 2 | 3.96 | | | | 0.04 | |
| 20 | $ZnGa_{1.96}Eu_{0.04}O_4$ | Ga 2% | 2 | 3.92 | | | | 0.08 | |
| 21 | $ZnGa_{1.92}Eu_{0.08}O_4$ | Ga 4% | 2 | 3.84 | | | | 0.16 | |
| 22 | $ZnGa_{1.88}Eu_{0.12}O_4$ | Ga 6% | 2 | 3.76 | | | | 0.24 | |
| 23 | $ZnGa_{1.80}Eu_{0.20}O_4$ | Ga 10% | 2 | 3.60 | | | | 0.40 | |
| 24 | $ZnGa_{1.98}Dy_{0.02}O_4$ | Ga 1% | 2 | 3.96 | | | | | 0.04 |
| 25 | $ZnGa_{1.94}Dy_{0.04}O_4$ | Ga 3% | 2 | 3.88 | | | | | 0.12 |
| 26 | $ZnGa_{1.88}Dy_{0.08}O_4$ | Ga 5% | 2 | 3.80 | | | | | 0.20 |

Final products of pure and metal doped zinc gallates were produced in batch sizes scaled from 10 milliliter (ml) in pressure tubes to 1 liter (L) in culture bottles. After two weeks, solid precipitated phosphors of zinc gallate spinel structures were harvested washed and used for characterization. In some instances, samples were processed through centrifugation, washing, and stored by mixing with methanol. The samples were then characterized using X-ray diffraction. Following characterization with X-ray diffraction, the doped zinc gallate spinel structures, i.e., sample numbers 2-26, were sintered at a temperature of 900° C. for a time period of 30 minutes in air and/or 30 min in inert gas if needed.

Flourescence and X-Ray Diffraction Patterns of Pure Zinc Gallate Structures

Figure 6:
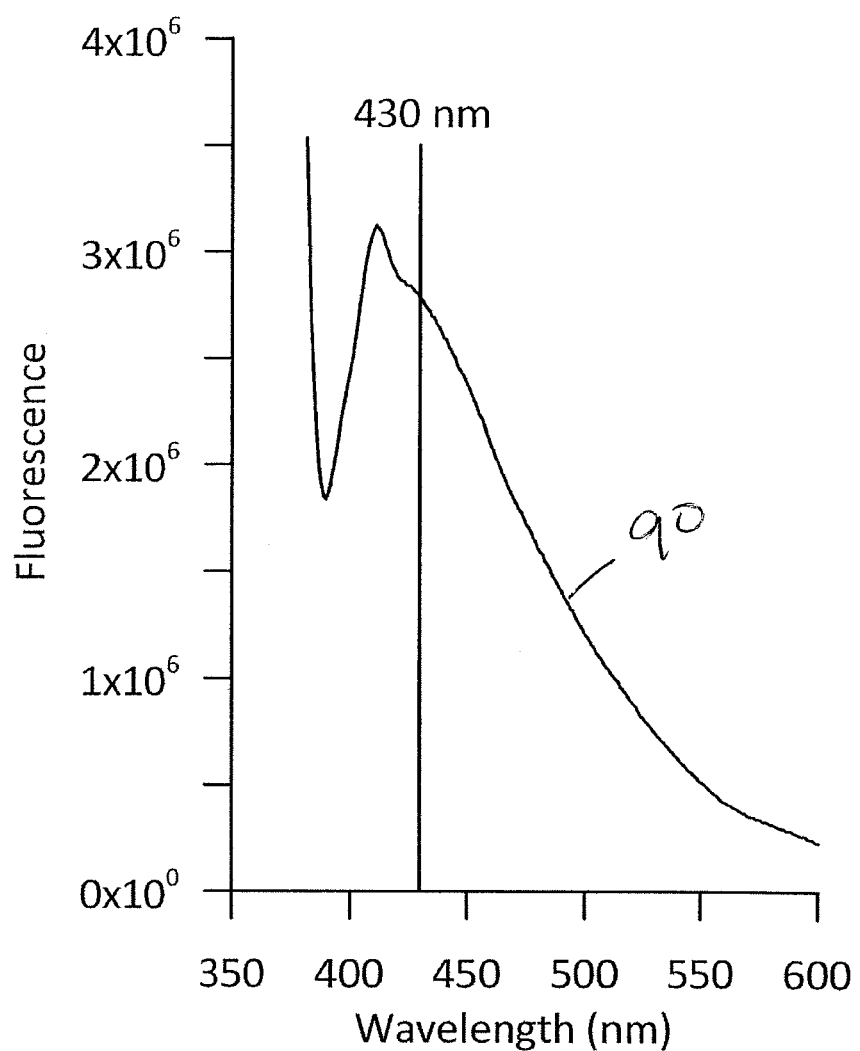
FIG. 6 is a plot of the fluorescence from one example of a pure zinc gallate spinel structure that was formed in accordance with the present disclosure.
Figure 7:
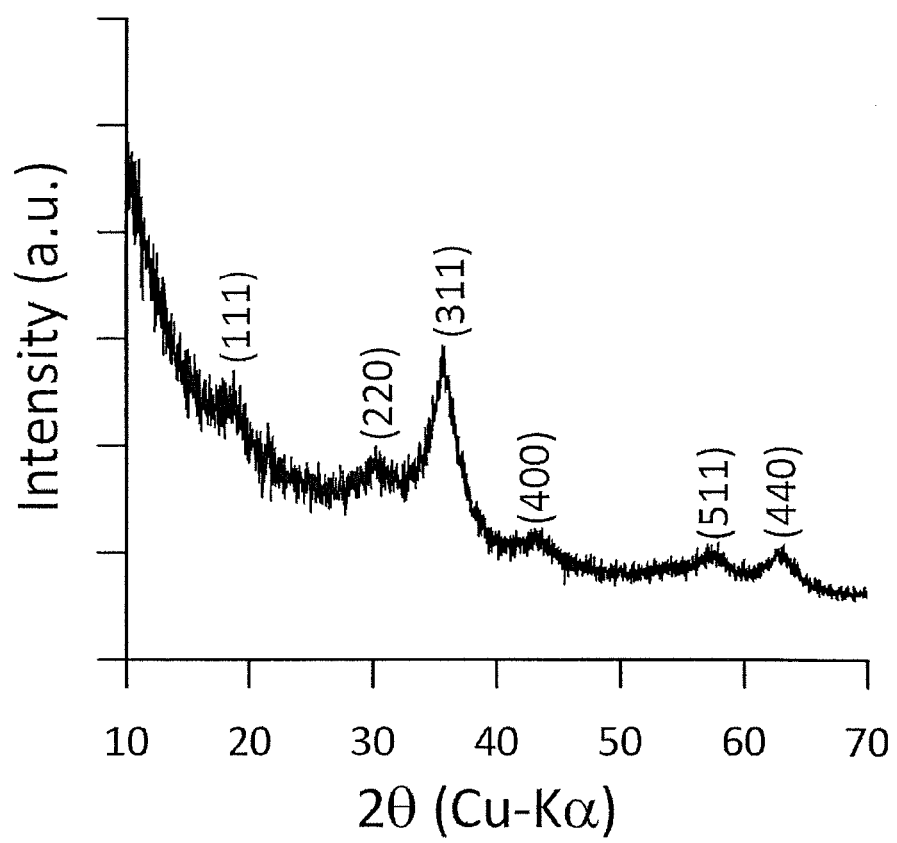
FIG. 7 is an X-ray diffraction pattern of one example of pure zinc gallate spinel structure that was formed in accordance with the present disclosure.

FIG. 6 is plot of the fluorescence of a pure zinc gallate spinel structure that exhibited an emission of light within the blue region of wavelengths. The composition of the pure zinc gallate spinel structure that provided data line 90, which is plotted in FIG. 6, is listed Table 1 and had a target composition of $ZnGa_2O_4$. The pure zinc gallate structure exhibited a peak fluorescence at a wavelength proximate to 430 nm in response to the application of UV light having a wavelength of 254 nm. FIG. 7 is an X-ray diffraction pattern taken from a pure zinc gallate spinel structure having the composition of sample 1 listed in Table 1.

Figure 8:
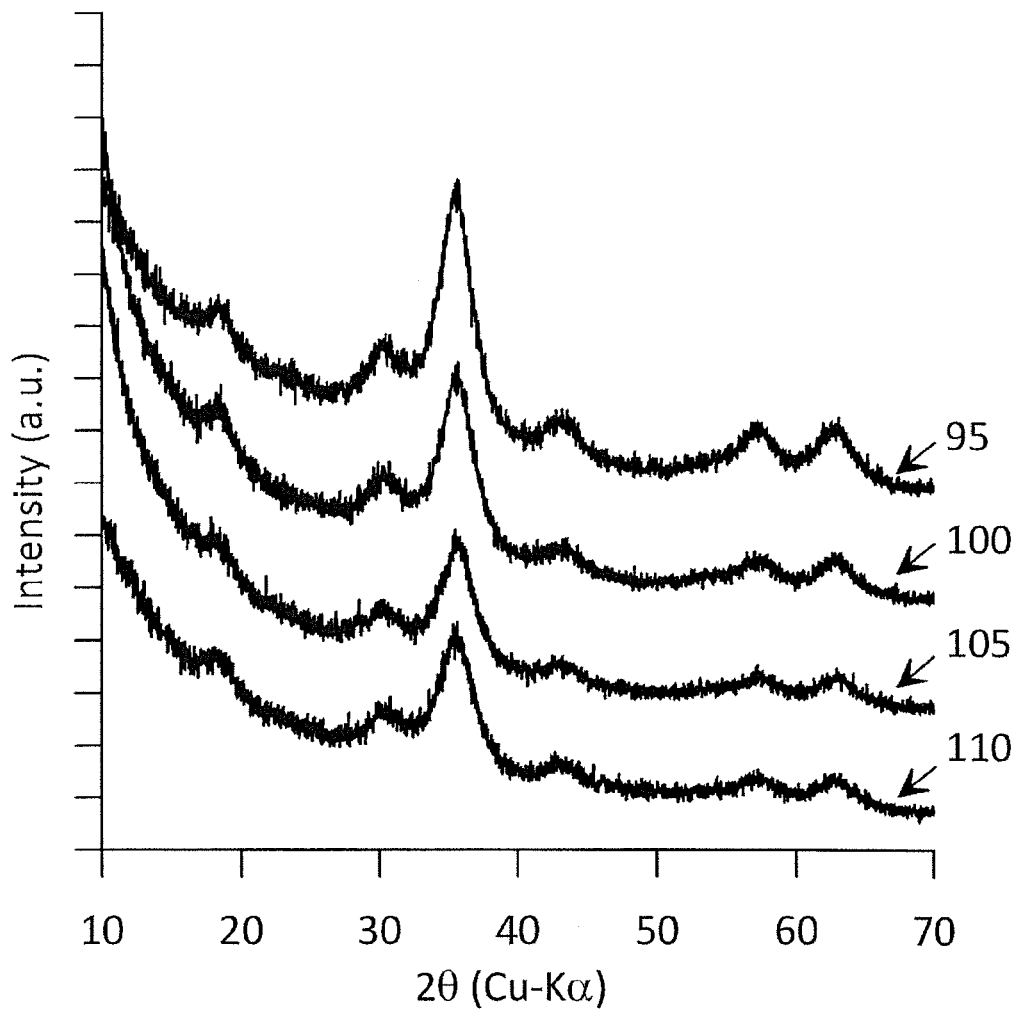
FIG. 8 depicts X-ray diffraction patterns for zinc gallate spinel structures that have been doped with cobalt, in accordance with one embodiment of the present disclosure.

Flourescence and X-Ray Diffraction Patterns of Zinc Gallate Structures Doped with Cobalt FIG. 8 is a plot of X-ray diffraction lines confirming that sample numbers 10-13 in Table 1 had a spinel crystal structure. Sample numbers 10-13 in Table 1 were a zinc gallate spinel structure that was doped with cobalt so that the cobalt was a substitutional dopant for zinc. Diffraction line 95 is the X-ray diffraction line taken from sample number 10 of Table 1, wherein the zinc gallate spinel structure was produced from the precursor solution equal to the target composition of $Zn_{0.99}Co_{0.01}Ga_2O_4$. Diffraction line 100 is the X-ray diffraction line taken from sample number 11 of Table 1, wherein the zinc gallate spinel structure was produced from the precursor solution equal to the target composition of $Zn_{0.98}Co_{0.02}Ga_2O_4$. Diffraction line 105 is the X-ray diffraction line taken from sample number 12 of Table 1, wherein the zinc gallate spinel structure was produced from the precursor solution equal to the target composition of $Zn_{0.96}Co_{0.04}Ga_2O_4$. Diffraction line 110 is the X-ray diffraction line taken from sample number 13 of Table 1, wherein the zinc gallate spinel structure was produced from the precursor solution equal to the target composition of $Zn_{0.94}Co_{0.06}Ga_2O_4$.

Figure 9:
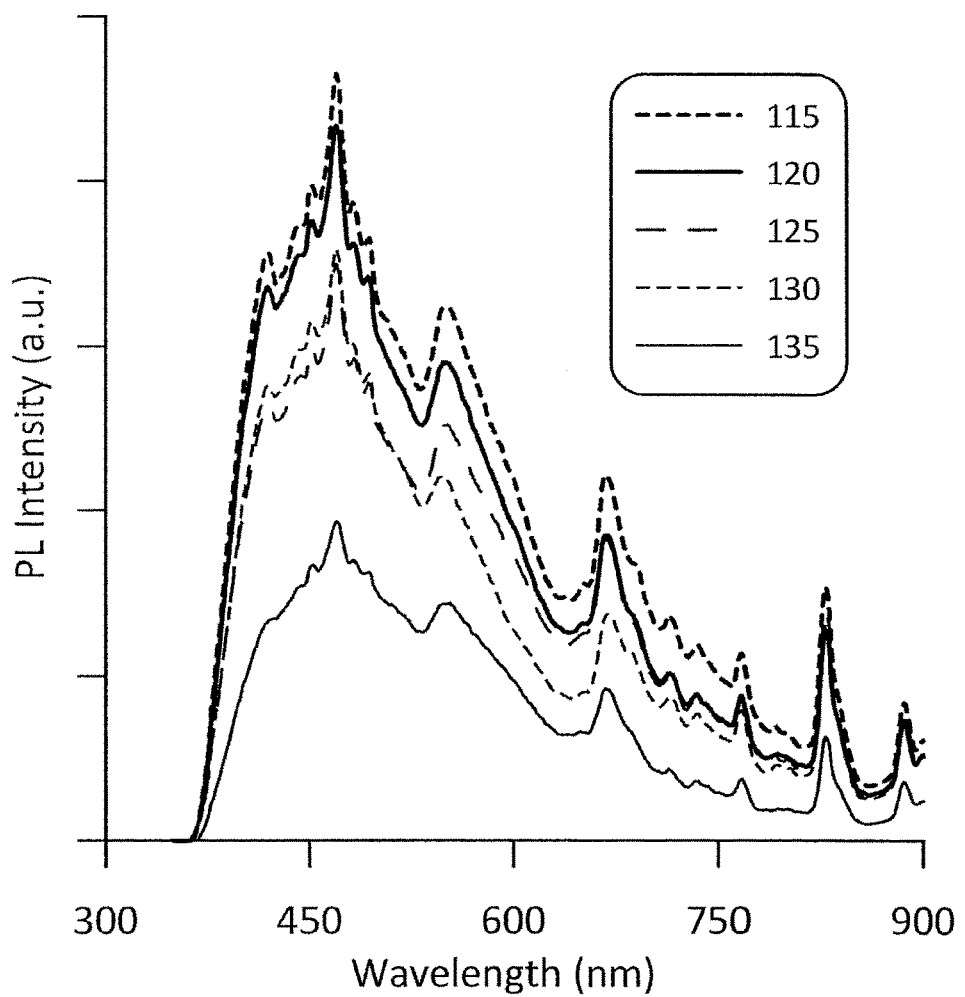
FIG. 9 is a plot of the fluorescence from zinc gallate spinel structure doped with cobalt in response to the application of ultraviolet light having a wavelength of 254 nm, in which the cobalt doped zinc gallate spinel structures were doped in accordance with the present disclosure.

FIG. 9 is a plot of the fluorescence from zinc gallate spinel structures doped with cobalt in response to the application of ultraviolet light having a wavelength of 254 nm. FIG. 9 depicts emission of wavelengths from the zinc gallate spinel structures doped with cobalt and pure zinc gallate spinel structures within the blue light spectrum. The zinc gallate spinel structures that provided the fluorescence plotted in FIG. 9 were doped zinc gallate spinel structures, in which cobalt was a substitution dopant with the zinc in the doped zinc gallate spinel structure. Data line 115 is a plot of the photoluminescence (PL) intensity measured from sample number 10 of Table 1, which was a zinc gallate spinel structure produced from the precursor solution equal to the target composition of $Zn_{0.99} Co_{0.01}Ga_2O_4$ (hereafter referred to as the zinc gallate spinel structure doped with 1% cobalt substituted for zinc). Data line 120 is a plot of the photoluminescence (PL) intensity measured from sample number 11 of Table 1 having a zinc gallate spinel structure produced from the precursor solution equal to the target composition of $Zn_{0.98} Co_{0.02}Ga_2O_4$ (hereafter referred to as the zinc gallate spinel structure doped with 2% cobalt substituted for zinc). Data line 125 is a plot of the photoluminescence (PL) intensity measured from sample number 12 of Table 1 having a zinc gallate spinel structure produced from the precursor solution equal to the target composition of $Zn_{0.96}Co_{0.04}Ga_2O_4$ (hereafter referred to as the zinc gallate spinel structure doped with 4% cobalt substituted for zinc). Data line 130 is a plot of the photoluminescence (PL) intensity measured from sample number 13 of Table 1 having a zinc gallate spinel structure produced from the precursor solution equal to the target composition of $Zn_{0.94}Co_{0.06}Ga_2O_4$ (hereafter referred to as the zinc gallate spinel structure doped with 6% cobalt substituted for zinc). Data line 135 is a plot of the photoluminescence (PL) intensity measured from sample number 1 of Table 1, which is a pure undoped zinc gallate structure having a zinc gallate spinel structure produced from the precursor solution equal to the target composition of $ZnGa_2O_4$. The pure undoped zinc gallate structures were not sintered. The peak wavelength of light emitted by the cobalt doped zinc gallate structures in response to the application of UV light having a wavelength of 254 nm that provided data lines 115, 120, 125, 130, 135 exhibited a peak fluorescence at a wavelength that was proximate to 430 nm.

The greatest photoluminescence (PL) intensity measured from the cobalt doped zinc gallate structures in response to the application of the ultraviolet light having the 254 nm wavelength was measured from the zinc gallate spinel structure doped with 1% cobalt substituted for zinc, as indicated by data line 115, followed by the zinc gallate spinel structure doped with 2% cobalt substituted for zinc, as indicated by data line 120. The cobalt doped zinc gallate spinel structures having the greater concentration of cobalt dopant, e.g., the zinc gallate spinel structure doped with 4% cobalt substituted for zinc depicted by data line 125 and the zinc gallate structure doped with 6% cobalt substituted for zinc depicted by data line 130, had a lower photoluminescence (PL) intensity. The pure undoped zinc gallate structure that provided data line 135 had a lower photoluminescence (PL) intensity when compared to the samples that were doped with cobalt as indicated by FIG. 9.

Figure 10:
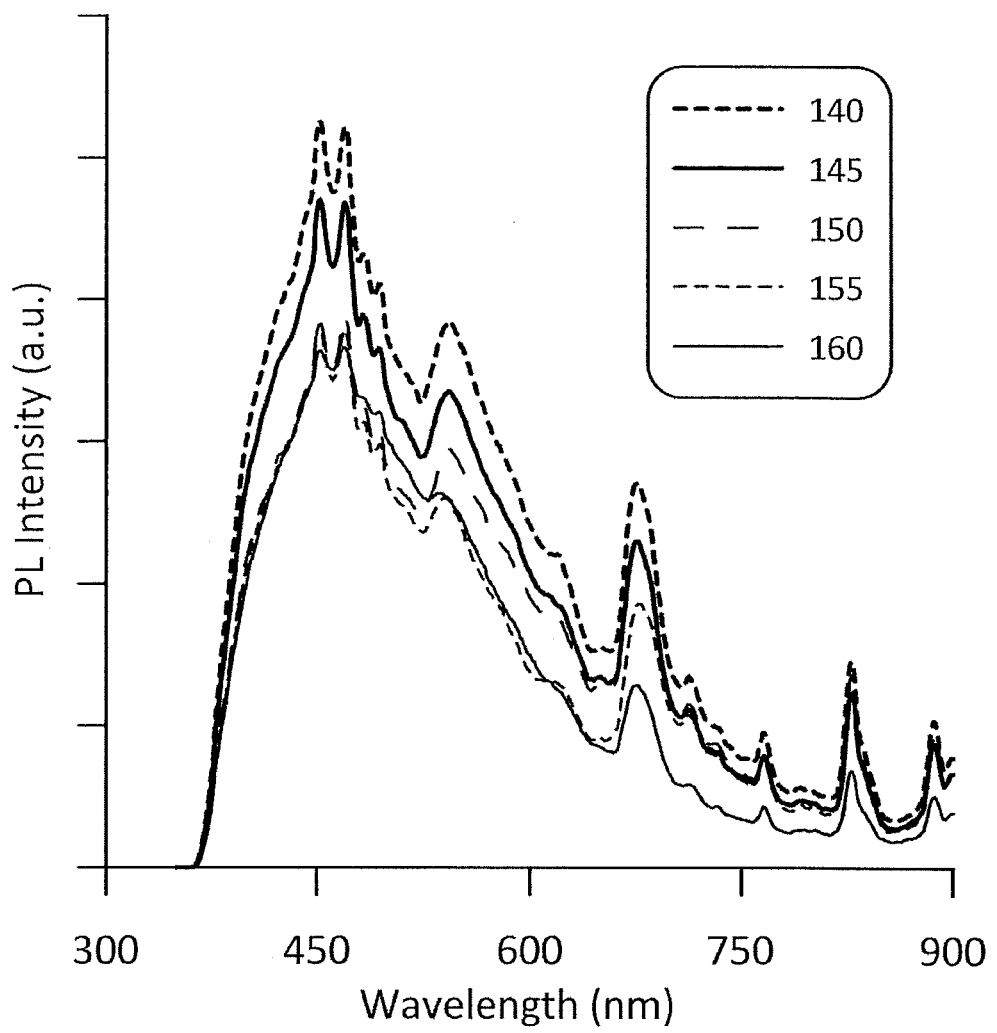
FIG. 10 is a plot of the fluorescence from zinc gallate spinel structure doped with cobalt in response to the application of ultraviolet light having a wavelength of 288 nm, in which the cobalt doped zinc gallate spinel structures were doped in accordance with the present disclosure.

FIG. 10 is a plot of the fluorescence from zinc gallate spinel structure doped with cobalt in response to the application of ultraviolet light having a wavelength of 288 nm. FIG. 10 depicts emission of wavelengths from the zinc gallate spinel structures doped with cobalt and pure zinc gallate spinel structures within the blue light spectrum. In FIG. 10, the cobalt is a substitution dopant with zinc in the doped zinc gallate spinel structure. Data line 140 is a plot of the photoluminescence (PL) intensity measured sample number 10 of Table 1, which was a zinc gallate spinel structure produced from the precursor solution equal to the target composition of $Zn_{0.99} Co_{0.01}Ga_2O_4$ (hereafter referred to as the zinc gallate spinel structure doped with 1% cobalt substituted for zinc). Data line 145 is a plot of the photoluminescence (PL) intensity measured from sample number 11 of Table 1 having a zinc gallate spinel structure produced from the precursor solution equal to the target composition of $Zn_{0.98}Co_{0.02}Ga_2O_4$ (hereafter referred to as the zinc gallate spinel structure doped with 2% cobalt substituted for zinc). Data line 150 is a plot of the photoluminescence (PL) intensity measured from sample number 12 of Table 1 having a zinc gallate spinel structure produced from the precursor solution equal to the target composition of $Zn_{0.96}Co_{0.04}Ga_2O_4$ (hereafter referred to as the zinc gallate spinel structure doped with 4% cobalt substituted for zinc). Data line 155 is a plot of the photoluminescence (PL) intensity measured from sample number 13 of Table 1 having a zinc gallate spinel structure produced from the precursor solution equal to the target composition of $Zn_{0.94}Co_{0.06}Ga_2O_4$ (hereafter referred to as the zinc gallate spinel structure doped with 6% cobalt substituted for zinc). Data line 160 is a plot of the photoluminescence (PL) intensity measured from sample number 1 of Table 1, which is a pure undoped zinc gallate structure produced from the precursor solution equal to the target composition of $ZnGa_2O_4$. The pure undoped zinc gallate structures that provided data line 160 were not sintered. The peak wavelength of light emitted by the cobalt doped zinc gallate structures in response to the application of UV light having a wavelength of 288 nm that provided data lines 140, 145, 150, 155, 160 exhibited a peak fluorescence at a wavelength that was proximate to 430 nm.

The greatest photoluminescence (PL) intensity by the cobalt doped zinc gallate structures in response to the application of the ultraviolet light having the 288 nm wavelength was measured from the zinc gallate spinel structure doped with 1% cobalt substituted for zinc, as indicated by data line 140, followed by the zinc gallate spinel structure doped with 2% cobalt substituted for zinc, as indicated by data line 145. The cobalt doped zinc gallate spinel structures having the greater concentration of cobalt dopant, e.g., the zinc gallate spinel structure doped with 4% cobalt substituted for zinc depicted by data line 150, and the zinc gallate spinel structure doped with 6% cobalt substituted for zinc depicted by data line 155, had a lower photoluminescence (PL) intensity. The pure undoped zinc gallate structure that provided data line 160 had a lower photoluminescence (PL) intensity when compared to the samples that were doped with cobalt as indicated by FIG. 10.

Figure 11:
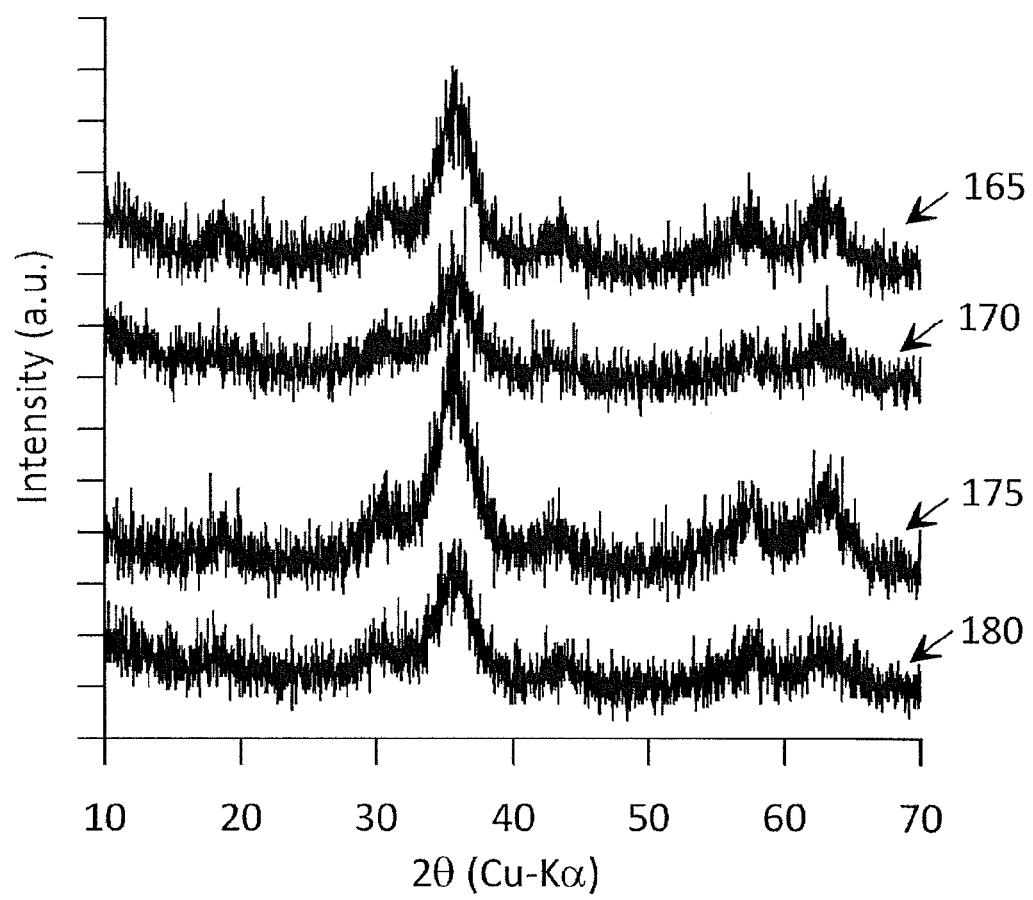
FIG. 11 depicts X-ray diffraction patterns for zinc gallate spinel structures that have been doped with manganese, in which the manganese is a substitutional dopant with zinc in the doped zinc gallate spinel structure, in accordance with one embodiment of the present disclosure.

Flourescence and X-Ray Diffraction Patterns of Zinc Gallate Structures Doped with Manganese FIG. 11 is a plot of X-ray diffraction lines confirming that sample numbers 2-5 in Table 1 had a spinel crystal structure. Sample numbers 2-5 where zinc gallate spinel structures that were doped with manganese so that the manganese is a substitutional dopant for zinc. Diffraction line 165 is the X-ray diffraction line taken from sample number 2 of Table 1, which was produced from the precursor solution equal to the target composition of $Zn_{0.99}Mn_{0.01}Ga_2O_4$. Diffraction line 170 is the X-ray diffraction line taken from sample number 3 of Table 1, which was produced from the precursor solution equal to the target composition of $Zn_{0.98}Mn_{0.02}Ga_2O_4$. Diffraction line 175 is the X-ray diffraction line taken from sample number 4 of Table 1, which was produced from the precursor solution equal to the target composition of $Zn_{0.96}Mn_{0.04}Ga_2O_4$. Diffraction line 180 is the X-ray diffraction line taken from sample number 5 of Table 1, which was produced from the precursor solution equal to the target composition of $Zn_{0.94}Mn_{0.06}Ga_2O_4$.

Figure 12:
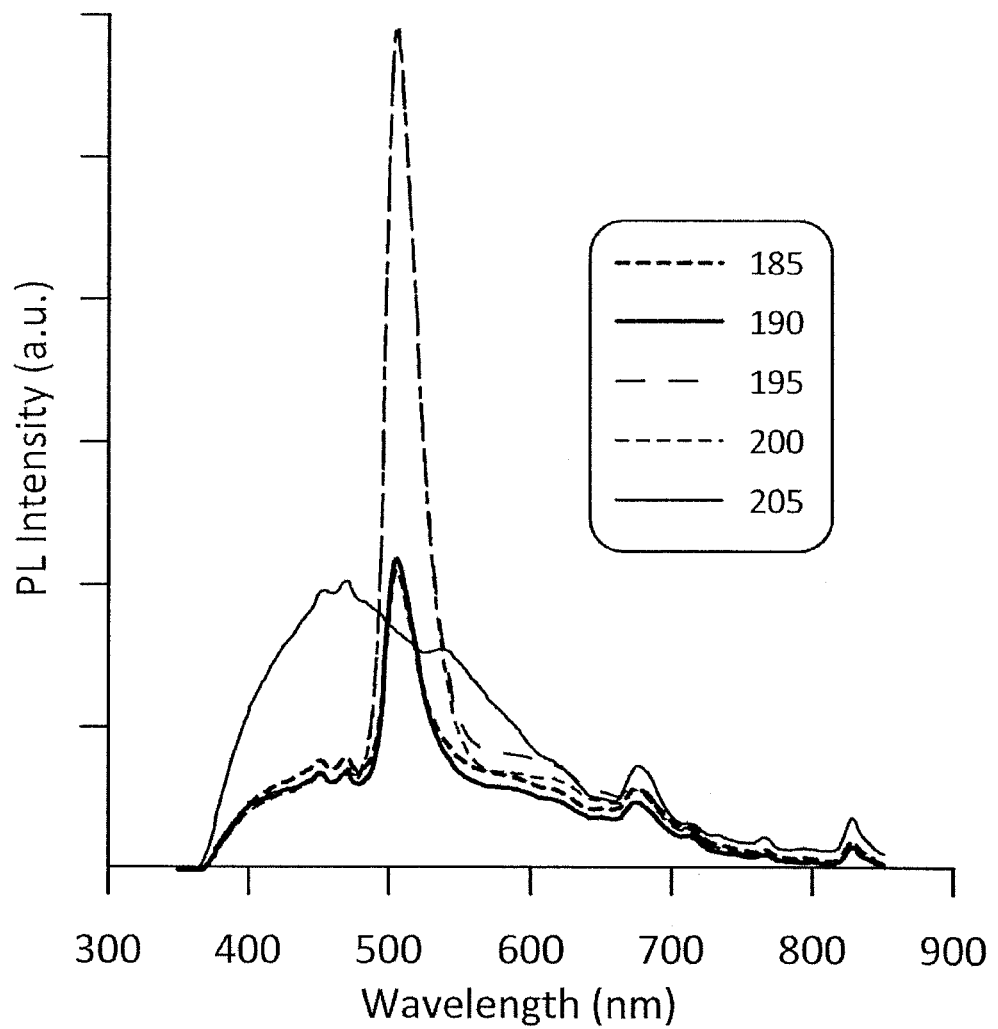
FIG. 12 is a plot of the fluorescence from zinc gallate spinel structure doped with manganese in response to the application of ultraviolet light having a wavelength of 288 nm, in which the manganese is a substitutional dopant for the zinc in the zinc gallate spinel structure, in accordance with one embodiment of the present disclosure.

FIG. 12 is a plot of the fluorescence from zinc gallate spinel structure doped with manganese in response to the application of ultraviolet light having a wavelength of 288 nm, in which the manganese was a substitutional dopant for the zinc in the zinc gallate spinel structure. FIG. 12 depicts emission of wavelengths from the zinc gallate spinel structures doped with manganese within the green light spectrum. In FIG. 12, the manganese is a substitution dopant with zinc in the doped zinc gallate spinel structure. Data line 185 is a plot of the photoluminescence (PL) intensity measured sample number 2 of Table 1, which was a zinc gallate spinel structure produced from the precursor solution equal to the target composition of $Zn_{0.99}Mn_{0.01}Ga_2O_4$ (hereafter referred to as a zinc gallate structure doped with 1% manganese substituted for zinc). Data line 190 is a plot of the photoluminescence (PL) intensity measured from sample number 3 of Table 1, which was produced from the precursor solution equal to the target composition of $Zn_{0.98}Mn_{0.02}Ga_2O_4$ (hereafter referred to as a zinc gallate structure doped with 2% manganese substituted for zinc). Data line 195 is a plot of the photoluminescence (PL) intensity measured from sample number 4 of Table 1, which was produced from the precursor solution equal to the target composition of $Zn_{0.96}Mn_{0.04}Ga_2O_4$ (hereafter referred to as a zinc gallate structure doped with 4% manganese substituted for zinc). Data line 200 is a plot of the photoluminescence (PL) intensity measured from sample number 5 of Table 1, which was produced from the precursor solution equal to the target composition of $Zn_{0.94}Mn_{0.06}Ga_2O_4$ (hereafter referred to as a zinc gallate structure doped with 6% manganese substituted for zinc). Data line 205 is a plot of the photoluminescence (PL) intensity measured from sample number 5 of Table 1, which is a pure undoped zinc gallate structure produced from the precursor solution equal to the target composition of $ZnGa_2O_4$. The pure undoped zinc gallate structures that provided data line 205 were not sintered. The peak wavelength of light emitted by the manganese doped zinc gallate structures in response to the application of UV light having a wavelength of 288 nm that provided data lines 185, 190, 195, and 200 exhibited a peak fluorescence at a wavelength that was proximate to 510 nm. In comparison, the undoped zinc gallate spinel structure that provided data line 205 exhibited a peak fluorescence at a wavelength that was proximate to 450 nm.

The greatest photoluminescence (PL) intensity by the doped zinc gallate structures having manganese substituted for zinc in response to the application of the ultraviolet light having the 288 nm wavelength was measured from the doped zinc gallate spinel structure with 6% manganese substituted for zinc, as indicated by data line 200, and the manganese doped zinc gallate spinel structure with 4% manganese substituted for zinc, as indicated by data line 195. The manganese doped zinc gallate spinel structures having the lower concentration of dopant, e.g., the doped zinc gallate structure with 2% manganese substituted for zinc depicted by data line 190 and the doped zinc gallate structure with 1% manganese substituted for zinc depicted by data line 185, had a lower photoluminescence (PL) intensity than the doped zinc gallate structures having the higher concentrations of manganese substituted for zinc. The pure undoped zinc gallate structure identified by data line 205 had the lowest photoluminescence (PL) intensity.

Figure 13:
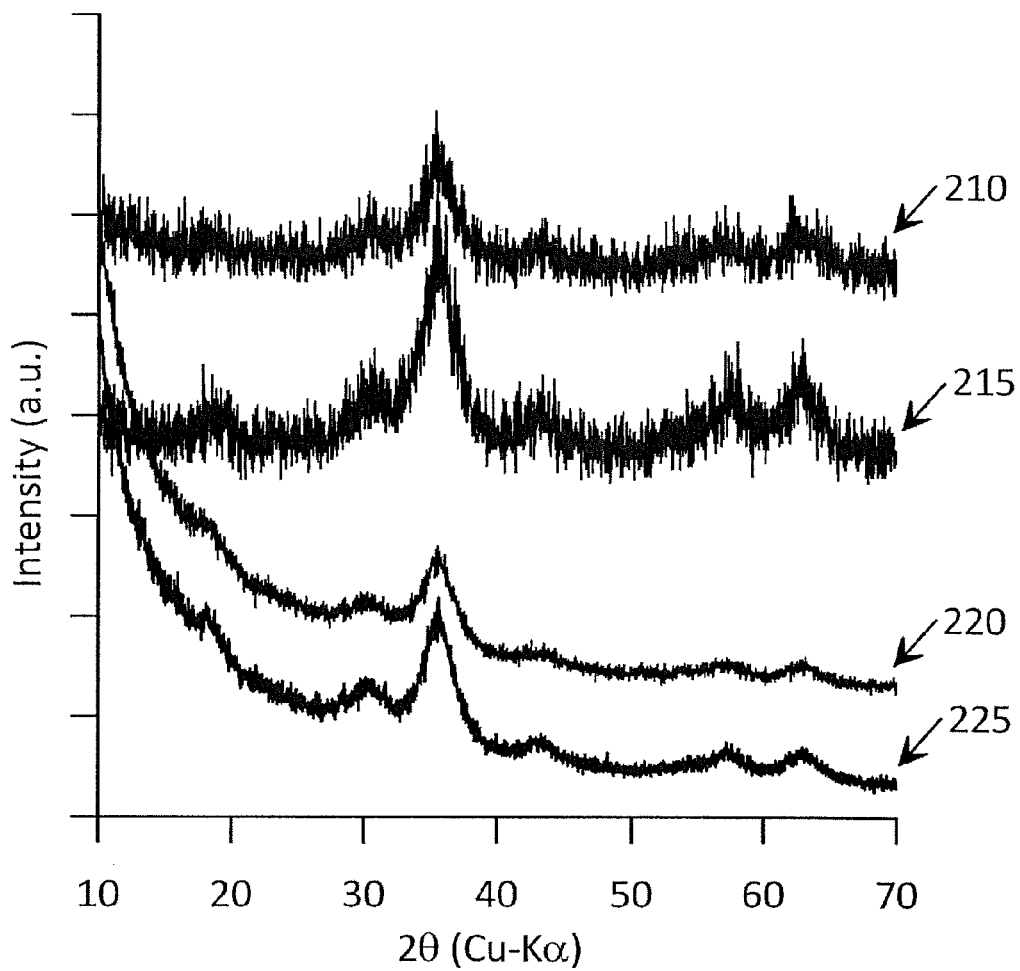
FIG. 13 depicts X-ray diffraction patterns for zinc gallate spinel structures that have been doped with manganese, in which the manganese is a substitutional dopant with gallium in the doped zinc gallate spinel structure, in accordance with one embodiment of the present disclosure.

FIG. 13 is a plot of X-ray diffraction lines confirming that sample numbers 6-9 in Table 1 had a spinel crystal structure. Sample numbers 6-9 were zinc gallate spinel structures that were doped with manganese so that the manganese was a substitutional dopant for gallium. Diffraction line 210 is the X-ray diffraction line taken from sample number 6 of Table 1, which was produced from the precursor solution equal to the target composition of $ZnGa_{1.98}Mn_{0.02}O_4$. Diffraction line 215 is the X-ray diffraction line taken from sample number 7 of Table 1, which was produced from the precursor solution equal to the target composition of $ZnGa_{1.96}Mn_{0.04}O_4$. Diffraction line 220 is the X-ray diffraction line taken from sample number 8 of Table 1, which was produced from the precursor solution equal to the target composition of $ZnGa_{1.92}Mn_{0.08}O_4$. Diffraction line 225 is the X-ray diffraction line taken from sample number 9 of Table 1, which was produced from the precursor solution equal to the target composition of $ZnGa_{1.88}Mn_{0.12}O_4$.

Figure 14:
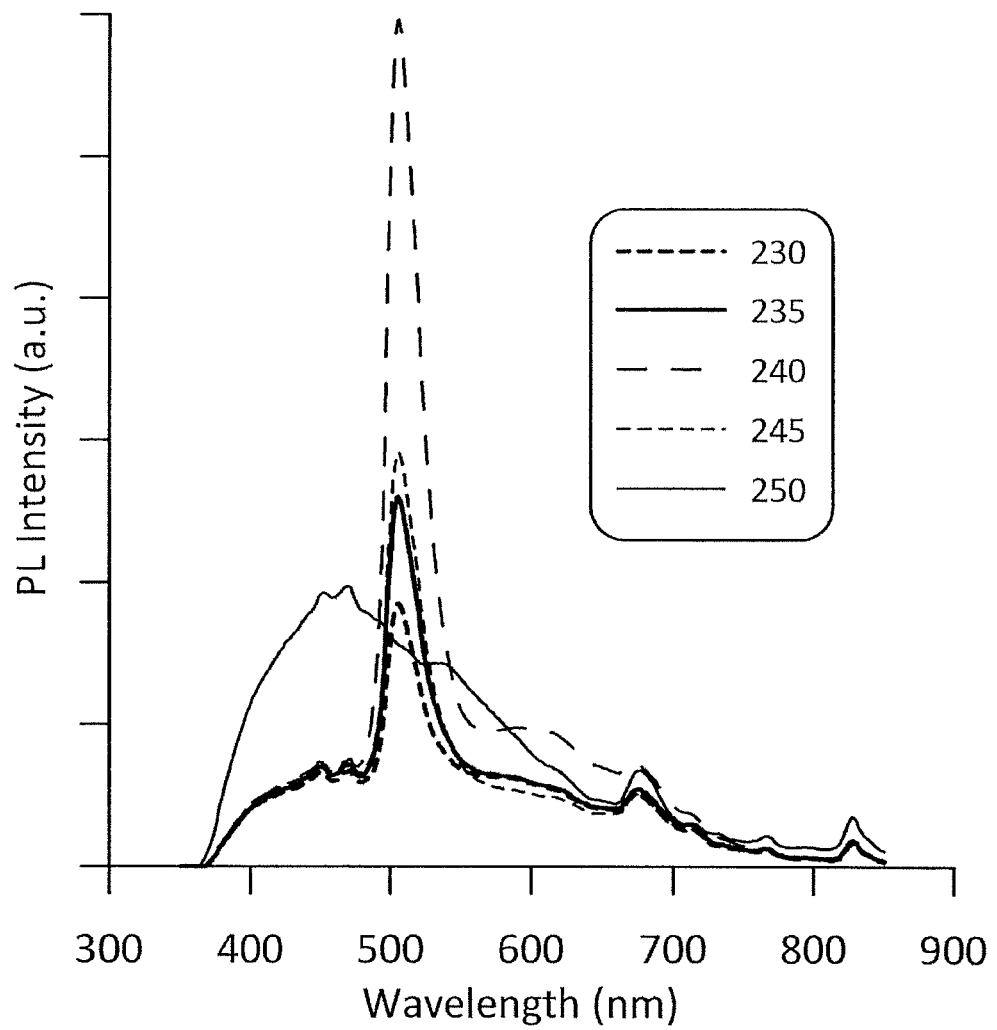
FIG. 14 is a plot of the fluorescence from zinc gallate spinel structure doped with manganese in response to the application of ultraviolet light having a wavelength of 288 nm, in which the manganese is a substitutional dopant for the gallium in the zinc gallate spinel structure, in accordance with one embodiment of the present disclosure.

FIG. 14 depicts emission of wavelengths measured from the zinc gallate spinel structures doped with manganese within the green light spectrum. In FIG. 14, the manganese was a substitution dopant with gallium in the doped zinc gallate spinel structure. Data line 230 is a plot of the photoluminescence (PL) intensity measured sample number 6 of Table 1, which was a zinc gallate spinel structure produced from the precursor solution equal to the target composition of $ZnGa_{1.98}Mn_{0.02}O_4$ (hereafter referred to as a zinc gallate structure doped with 1% manganese substituted for gallium). Data line 235 is a plot of the photoluminescence (PL) intensity measured from sample number 7 of Table 1, which was a zinc gallate spinel structure produced from the precursor solution equal to the target composition of (hereafter referred to as a zinc gallate structure doped with 2% manganese substituted for gallium). Data line 240 is a plot of the photoluminescence (PL) intensity measured from sample number 4 of Table 1, which was a zinc gallate spinel structure produced from the precursor solution equal to the target composition of $ZnGa_{1.92}Mn_{0.08}O_4$ (hereafter referred to as a zinc gallate structure doped with 4% manganese substituted for gallium). Data line 245 is a plot of the photoluminescence (PL) intensity measured from sample number 5 of Table 1, which was a zinc gallate spinel structure produced from the precursor solution equal to the target composition of $ZnGa_{1.88}Mn_{0.12}O_4$ (hereafter referred to as a zinc gallate structure doped with 6% manganese substituted for gallium). Data line 250 is a plot of the photoluminescence (PL) intensity measured from sample number 5 of Table 1, which is a pure undoped zinc gallate structure produced from the precursor solution equal to the target composition of $ZnGa_2O_4$. The pure undoped zinc gallate structures that provided data line 250 were not sintered. The peak wavelength of light emitted by the manganese doped zinc gallate structures, in which manganese was substituted with gallium, in response to the application of UV light having a wavelength of 288 nm that provided data lines 230, 235, 240, and 245 exhibited a peak fluorescence at a wavelength that was proximate to 510 nm. In comparison, the undoped zinc gallate spinel structure that provided data line 250 exhibited a peak fluorescence at a wavelength that was proximate to 450 nm.

The greatest photoluminescence (PL) intensity by the doped zinc gallate structures having manganese substituted for gallium in response to the application of the ultraviolet light having the 288 nm wavelength was measured from the zinc gallate structure doped with 4% manganese substituted for gallium, as indicated by data line 240, and the zinc gallate structure doped with 6% manganese substituted for gallium, as indicated by data line 245. The manganese doped zinc gallate spinel structures having the lower concentration of dopant, e.g., the zinc gallate structure doped with 2% manganese substituted for gallium depicted by data line 230 and the zinc gallate structure doped with 1% manganese substituted for gallium depicted by data line 235, had a lower photoluminescence (PL) intensity than the doped zinc gallate structures having the higher concentrations of manganese substituted for gallium. The pure undoped zinc gallate structure identified by data line 205 had a lower photoluminescence (PL) intensity than the doped zinc gallate structures with the exception of the zinc gallate structure doped with 1% manganese substituted for gallium.

Figure 15:
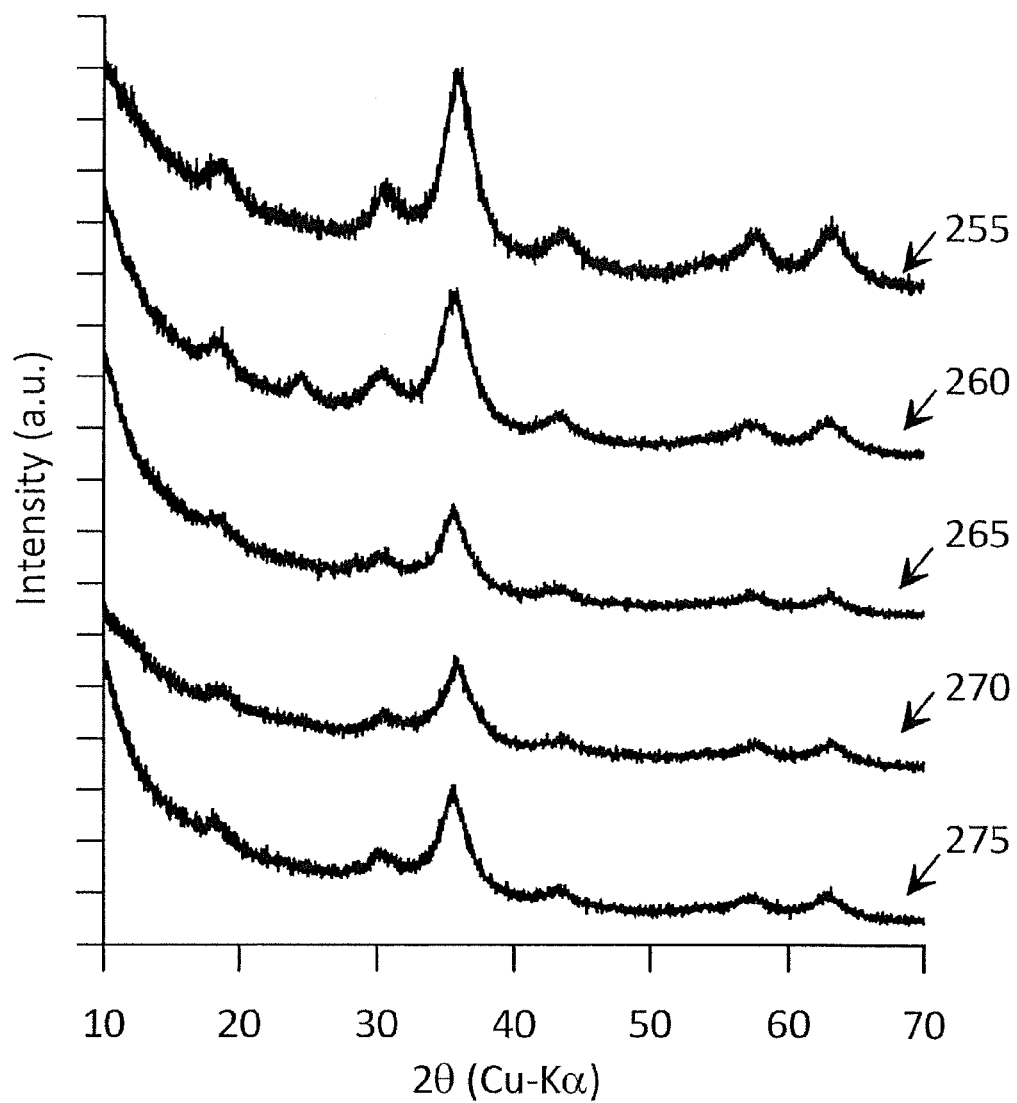
FIG. 15 depicts X-ray diffraction patterns for zinc gallate spinel structures that have been doped with chromium, in which the chromium is a substitutional dopant with gallium in the doped zinc gallate spinel structure, in accordance with one embodiment of the present disclosure.

Flourescence and X-Ray Diffraction Patterns of Zinc Gallate Structures Doped with Chromium FIG. 15 is a plot of X-ray diffraction lines confirming that sample numbers 14-18 in Table 1 had a spinel crystal structure. Sample numbers 14-18 were zinc gallate spinel structures that were doped with chromium so that the chromium was a substitutional dopant for gallium. Diffraction line 255 is the X-ray diffraction line taken from sample number 14 of Table 1, which was produced from the precursor solution equal to the target composition of $ZnGa_{1.98}Cr_{0.02}O_4$. Diffraction line 260 is the X-ray diffraction line taken from sample number 15 of Table 1, which was produced from the precursor solution equal to the target composition of $ZnGa_{1.96}Cr_{0.04}O_4$. Diffraction line 265 is the X-ray diffraction line taken from sample number 16 of Table 1, which was produced from the precursor solution equal to the target composition of $ZnGa_{1.92}Cr_{0.08}O_4$. Diffraction line 270 is the X-ray diffraction line taken from sample number 17 of Table 1, which was produced from the precursor solution equal to the target composition of $ZnGa_{1.88}Cr_{0.12}O_4$. Diffraction line 275 is the X-ray diffraction line taken from sample number 18 of Table 1, which was produced from the precursor solution equal to the target composition of $ZnGa_{1.80}Cr_{0.20}O_4$.

Figure 16:
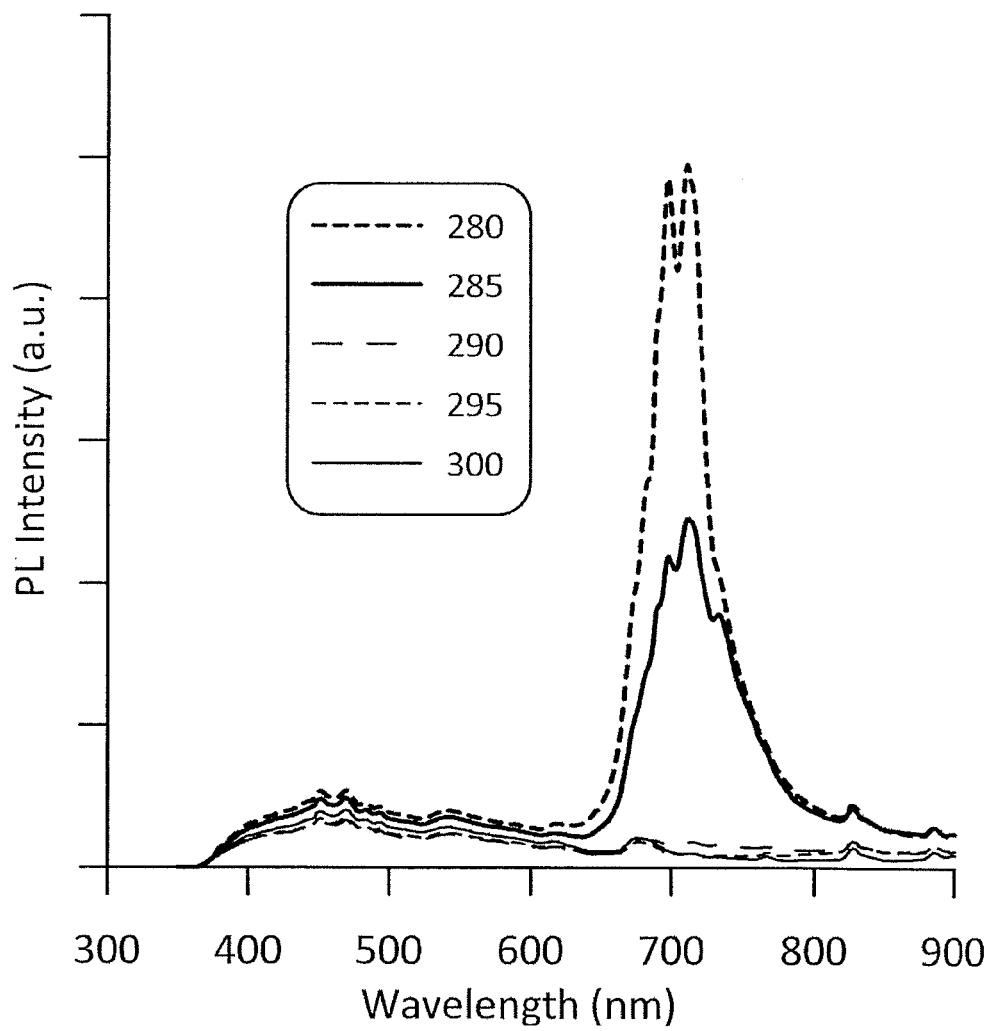
FIG. 16 is a plot of the fluorescence from zinc gallate spinel structure doped with chromium in response to the application of ultraviolet light having a wavelength of 288 nm, in which the chromium is a substitutional dopant for the gallium in the zinc gallate spinel structure, in accordance with one embodiment of the present disclosure.

FIG. 16 is a plot of the fluorescence from zinc gallate spinel structure doped with chromium in response to the application of ultraviolet light having a wavelength of 288 nm, in which the chromium was a substitutional dopant for the zinc in the zinc gallate spinel structure. FIG. 16 depicts emission of wavelengths from the zinc gallate spinel structures doped with chromium within the red light spectrum. Data line 280 is a plot of the photoluminescence (PL) intensity measured sample number 14 of Table 1, which was a zinc gallate spinel structure produced from the precursor solution equal to the target composition of $ZnGa_{1.98}Cr_{0.02}O_4$ (hereafter referred to as a zinc gallate structure doped with 1% chromium substituted for gallium). Data line 285 is a plot of the photoluminescence (PL) intensity measured from sample number 15 of Table 1 produced from the precursor solution equal to the target composition of $ZnGa_{1.96}Cr_{0.04}O_4$ (hereafter referred to as a zinc gallate structure doped with 2% chromium substituted for gallium). Data line 290 is a plot of the photoluminescence (PL) intensity measured from sample number 16 of Table 1 produced from the precursor solution equal to the target composition of $ZnGa_{1.92}Cr_{0.08}O_4$ (hereafter referred to as a zinc gallate structure doped with 4% chromium substituted for gallium). Data line 295 is a plot of the photoluminescence (PL) intensity measured from sample number 17 of Table 1 produced from the precursor solution equal to the target composition of $ZnGa_{1.88}Cr_{0.12}O_4$ (hereafter referred to as a zinc gallate structure doped with 6% chromium substituted for gallium). Data line 300 is a plot of the photoluminescence (PL) intensity measured from sample number 10 of Table 1 produced from the precursor solution equal to the target composition of $ZnGa_{1.80}Cr_{0.20}O_4$ (hereafter referred to as a zinc gallate structure doped with 10% chromium substituted for gallium). The peak wavelength of light emitted by the chromium doped zinc gallate structures in response to the application of UV light having a wavelength of 288, such as the peak wavelength illustrated by data lines 280 and 285, was proximate to 700 nm.

The greatest photoluminescence (PL) intensity by the doped zinc gallate structures having chromium substituted for gallium in response to the application of the ultraviolet light having the 288 nm wavelength was measured from the zinc gallate spinel structure doped with 1% chromium substituted for gallium, as indicated by data line 280, and zinc gallate spinel structure doped with 2% chromium substituted for gallium, as indicated by data line 285. The chromium doped zinc gallate spinel structures having greater concentrations of dopant, e.g., the zinc gallate structure doped with 4% chromium substituted for gallium depicted by data line 290, the zinc gallate structure doped with 6% chromium substituted for gallium depicted by data line 295, and the doped zinc gallate structure with 10% chromium substituted for gallium depicted by data line 300 did not show distinct emission peak in the red region.

Figure 17:
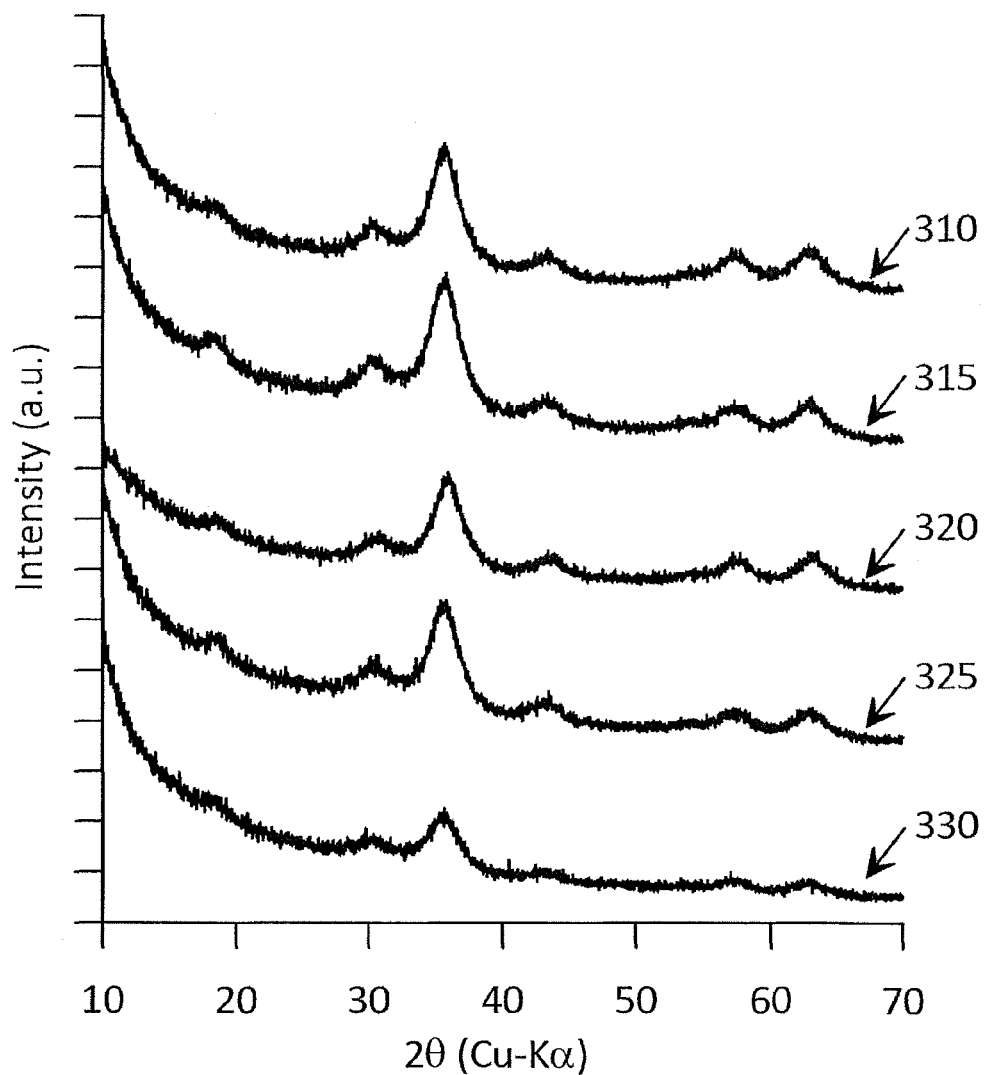
FIG. 17 depicts X-ray diffraction patterns for zinc gallate spinel structures that have been doped with europium, in which the europium is a substitutional dopant with gallium in the doped zinc gallate spinel structure, in accordance with one embodiment of the present disclosure.

Flourescence and X-Ray Diffraction Patterns of Zinc Gallate Structures Doped with Europium FIG. 17 is a plot of X-ray diffraction lines confirming that sample numbers 19-23 in Table 1 had a spinel crystal structure. Sample numbers 19-23 were zinc gallate spinel structure that were doped with europium so that the europium was a substitutional dopant for gallium. Diffraction line 310 is the X-ray diffraction line taken from sample number 19 of Table 1, which was produced from the precursor solution equal to the target composition of $ZnGa_{1.98}Eu_{0.02}O_4$. Diffraction line 315 is the X-ray diffraction line taken from sample number 20 of Table 1, which was produced from the precursor solution equal to the target composition of $ZnGa_{1.96}Eu_{0.04}O_4$. Diffraction line 320 is the X-ray diffraction line taken from sample number 21 of Table 1, which was produced from the precursor solution equal to the target composition of $ZnGa_{1.92}Eu_{0.08}O_4$. Diffraction line 325 is the X-ray diffraction line taken from sample number 22 of Table 1, which was produced from the precursor solution equal to the target composition of $ZnGa_{1.88}Eu_{0.12}O_4$. Diffraction line 330 is the X-ray diffraction line taken from sample number 23 of Table 1, which was produced from the precursor solution equal to the target composition of $ZnGa_{1.80}Eu_{0.20}O_4$.

Figure 18:
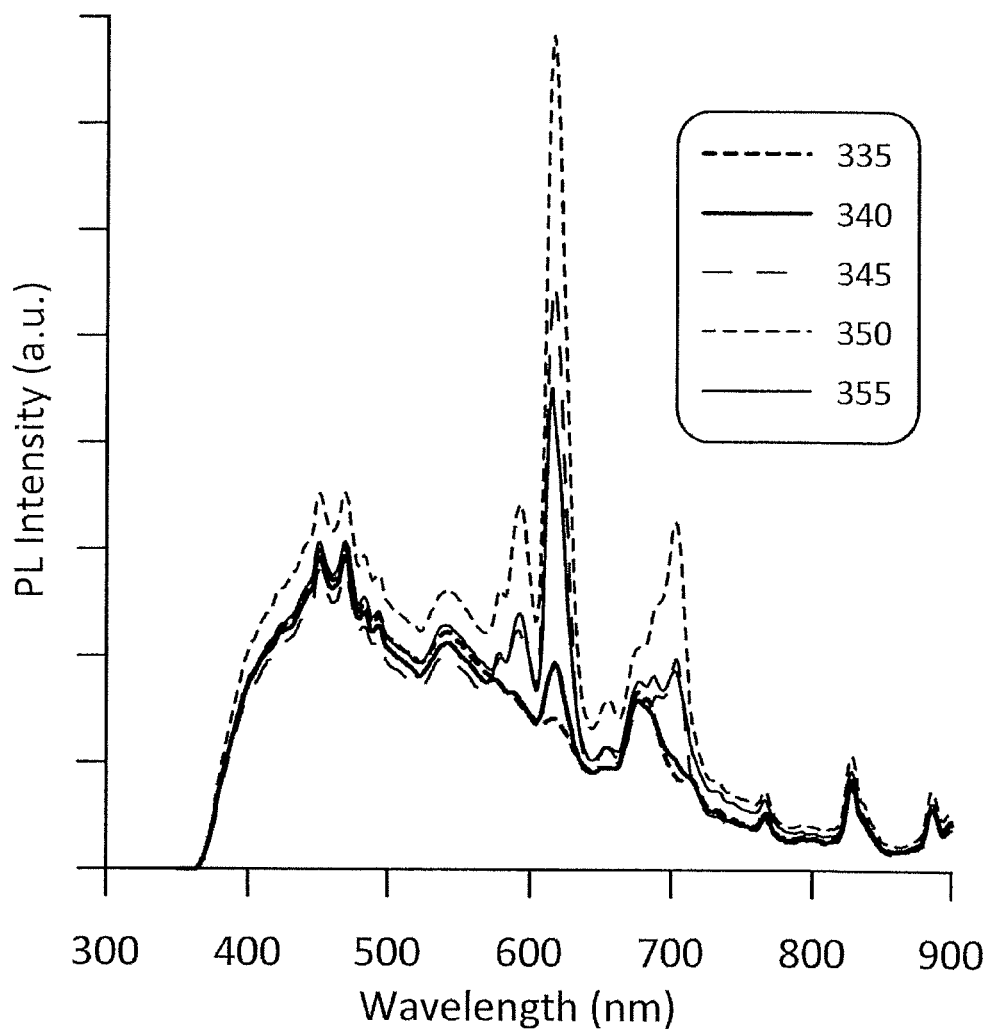
FIG. 18 is a plot of the fluorescence from zinc gallate spinel structure doped with europium in response to the application of ultraviolet light having a wavelength of 288 nm, in which the europium is a substitutional dopant for the gallium in the zinc gallate spinel structure, in accordance with one embodiment of the present disclosure.

FIG. 18 is a plot of the fluorescence from zinc gallate spinel structure doped with europium in response to the application of ultraviolet light having a wavelength of 288 nm, in which the europium was a substitutional dopant for the gallium in the zinc gallate spinel structure. FIG. 18 depicts emission of wavelengths from the zinc gallate spinel structures doped with europium within the red light spectrum. Data line 335 is a plot of the photoluminescence (PL) intensity measured from sample number 19 of Table 1, which was a zinc gallate spinel structure produced from the precursor solution equal to the target composition of to $ZnGa_{1.98}Eu_{0.02}O_4$ (hereafter referred to as a zinc gallate structure doped with 1% europium substituted for gallium). Data line 340 is a plot of the photoluminescence (PL) intensity measured from sample number 20 of Table 1 produced from the precursor solution equal to the target composition of $ZnGa_{1.96}Eu_{0.04}O_4$ (hereafter referred to as a zinc gallate structure doped with 2% europium substituted for gallium). Data line 345 is a plot of the photoluminescence (PL) intensity measured from sample number 21 of Table 1 produced from the precursor solution equal to the target composition of $ZnGa_{1.92}Eu_{0.08}O_4$ (hereafter referred to as a zinc gallate structure doped with 4% europium substituted for gallium). Data line 350 is a plot of the photoluminescence (PL) intensity measured from sample number 22 of Table 1 produced from the precursor solution equal to the target composition of $ZnGa_{1.88}Cr_{0.12}O_4$ (hereafter referred to as a zinc gallate structure doped with 6% europium substituted for gallium). Data line 300 is a plot of the photoluminescence (PL) intensity measured from sample number 23 of Table 1 produced from the precursor solution equal to the target composition of $ZnGa_{1.80}Eu_{0.20}O_4$ (hereafter referred to as a zinc gallate structure doped with 10% europium substituted for gallium). The peak wavelength of light emitted by the chromium doped zinc gallate structures in response to the application of UV light having a wavelength of 288, such as the peak wavelength illustrated by data lines 345, 350 and 355, was proximate to 625 nm.

The greatest photoluminescence (PL) intensity by the doped zinc gallate structures having europium substituted for gallium in response to the application of the ultraviolet light having the 288 nm wavelength was measured from the doped zinc gallate spinel structure with 6% europium substituted for gallium, as indicated by data line 350, and doped zinc gallate spinel structure with 4% europium substituted for gallium, as indicated by data line 345. Following the intensity of the doped zinc gallate spinel structure with 4% europium substituted for gallium, the next highest intensity was measured from doped zinc gallate spinel structure with 10% europium substituted for gallium, as indicated by data line 355. The europium doped zinc gallate spinel structures having concentrations of dopant less than 4%, such as the doped zinc gallate structure with 2% europium substituted for gallium depicted by data line 340 and the doped zinc gallate structure with 1% europium substituted for gallium depicted by data line 330, had a lower photoluminescence (PL) intensity than the doped zinc gallate structures having concentrations of dopant greater than 4%. A second peak wavelength of light emission at approximately 450 nm was measured from each of the europium doped zinc gallate spinel structures, which was attributed to the wavelength of light emitted from the host material, i.e., undoped zinc gallate structure.

Figure 19:
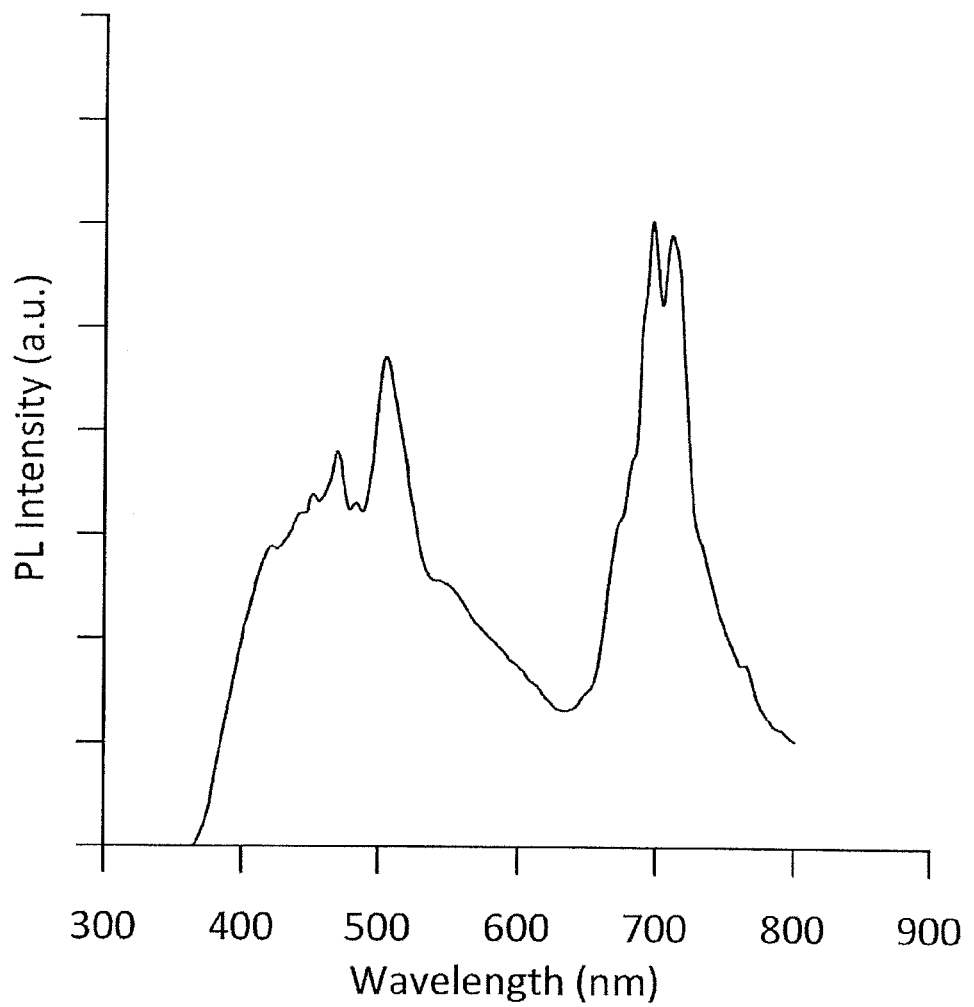
FIG. 19 is a plot of the fluorescence from a mixture of doped zinc gallate spinel in response to the application of ultraviolet light having a wavelength of 254 nm, in accordance with one embodiment of the present disclosure.

Flourescence of a Mixture of Doped Zinc Gallate Structures Doped to Produce White Light FIG. 19 is a plot of the fluorescence from a mixture of doped zinc gallate spinel structures in response to the application of ultraviolet light having a wavelength of 254 nm. The mixture of doped zinc gallate spinel structures included a manganese doped zinc gallate structure having a target composition equal to sample number 4, i.e., $Zn_{0.96}Mn_{0.04}Ga_2O_4$, of Table 1, a chromium doped zinc gallate spinel structure having a target composition equal to sample number 14, i.e., $Zn Ga_{1.98}Cr_{0.02}O_4$, of Table 1, and a cobalt doped zinc gallate spinel structure having a composition equal to sample number 10, i.e., $Zn_{0.99}Co_{0.01}Ga_2O_4$, of Table 1. The mixture included 50 wt. % cobalt doped zinc gallate spinel structure, 30 wt. % manganese doped zinc gallate structure, and 20 wt. % chromium doped zinc gallate spinel structure. The mixture of doped zinc gallate spinel structures emitted white light in response to the application of ultraviolet light having a wavelength of 254 nm. Referring to FIG. 19, the wavelength peak at approximately 475 nm was provide by the cobalt doped zinc gallate spinel structure portion of the mixture, the wavelength peak at approximately 510 nm was provided by the manganese doped zinc gallate structure portion of the mixture, and the wavelength peak at approximately 700 nm was provided by the chromium doped zinc gallate spinel structure portion of the mixture.

Preparation and Flourescence of a Copper Gallate ($CuGa_2O_4$)

Figure 20:
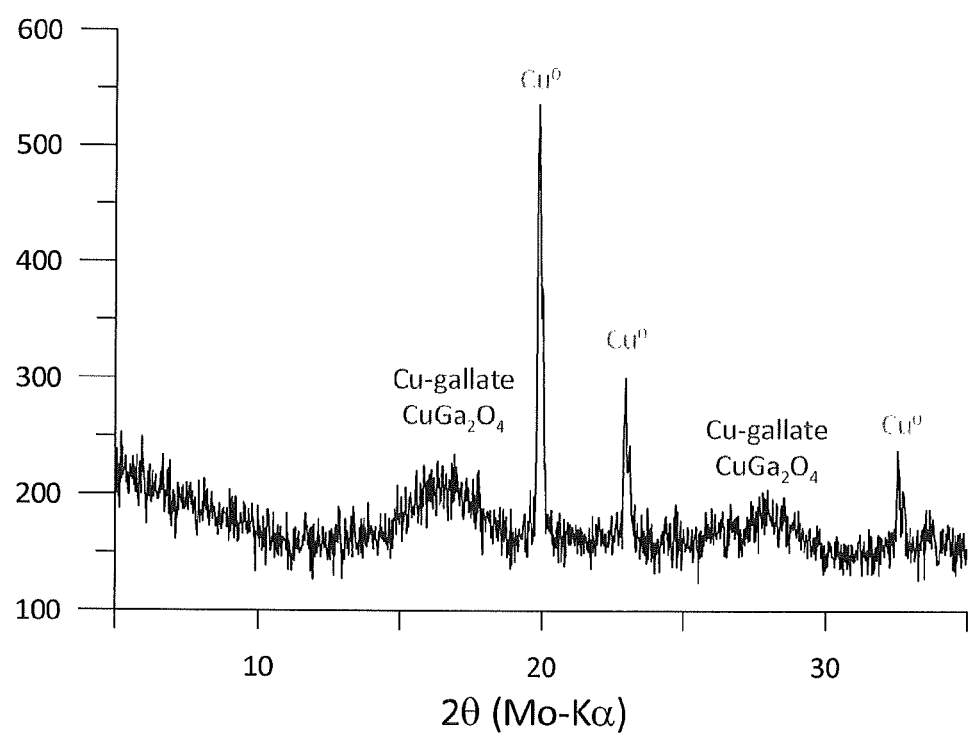
FIG. 20 shows an X-ray diffraction pattern for copper gallate spinel structures produced by the microbial method described herein.

Copper gallate nanoparticles were microbially produced in a manner analogous to the above-described process for the production of zinc gallate nanoparticles. In the process, 2 mM of a copper salt and 4 mM of a gallium-containing salt were contacted with bacteria to produce copper gallate nanoparticles of ~5 nm. A relatively larger amount of elemental copper ($Cu^0$) impurity having a size of around 90 nm was also observed. FIG. 20 shows the X-ray diffraction pattern for the copper gallate spinel structures. The X-ray diffraction pattern shows the presence of copper gallate and elemental copper.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of forming a metal gallate spinel structure, the method comprising:
   providing a supply of fermentative or thermophilic bacteria;
   reacting a divalent metal-containing salt and a gallium-containing salt with the supply of fermentative or thermophilic bacteria, wherein treatment of the divalent metal-containing salt and the gallium-containing salt with the fermentative or thermophilic bacteria nucleates a divalent metal gallate spinel structure.

2. The method of claim 1, further comprising including at least one dopant in the presence of said divalent metal-containing salt, gallium-containing salt and fermentative or thermophilic bacteria to nucleate a divalent metal gallate spinel structure containing said at least one dopant.

3. The method of claim 1, wherein the fermentative or thermophilic bacteria comprises *Thermoanaerobacter* bacteria.

4. The method of claim 1, wherein the divalent metal-containing salt, the gallium-containing salt and the supply of fermentative or thermophilic bacteria are contained in an aqueous solution.

5. The method of claim 1, wherein a zinc gallate spinel structure is formed by selecting the divalent metal-containing salt as a zinc-containing salt, wherein treatment of the zinc-containing salt and the gallium-containing salt with the fermentative or thermophilic bacteria nucleates a zinc gallate spinel structure.

6. The method of claim 5, further comprising including at least one dopant in the presence of said zinc-containing salt, gallium-containing salt and fermentative or thermophilic bacteria to nucleate a zinc gallate spinel structure containing said at least one dopant.

7. The method of claim 5, wherein the zinc-containing salt is selected from zinc chloride ($ZnCl_2$), zinc bromide ($ZnBr_2$), zinc nitrate hydrate ($Zn(NO_3)_2.xH_2O$), zinc sulfate hydrate ($ZnSO_4.xH_2O$), zinc phosphate ($Zn_3(PO_4)_2$), zinc acetate hydrate ($((CH_3CO_2)_2Zn).xH_2O$), zinc stearate ($[CH_3(CH_2)_{16}COO]_2Zn$), zinc fluoride ($ZnF_2$), zinc iodide ($ZnI_2$), zinc methoxide ($C_2H_6O_2Zn$), zinc acrylate ($(H_2C=CHCO_2)_2Zn$), and combinations thereof.

8. The method of claim 1, wherein the gallium-containing salt is selected from gallium chloride ($GaCl_3$), gallium chloride ($GaCl_2$), gallium nitrate hydroxide ($GaNO_3.xH_2O$), gallium fluoride ($GaF_3$), gallium iodide ($GaI_3$), gallium bromide ($GaBr_3$), gallium sulfate hydrate ($GaSO_4.xH_2O$), and combinations thereof.

9. The method of claim 5, wherein the zinc gallate spinel structure is $ZnGa_2O_4$.

10. The method of claim 1, wherein the treatment of the divalent metal-containing salt and the gallium-containing salt with the fermentative or thermophilic bacteria to nucleate the divalent metal gallate spinel structure comprises adjusting a pH of a solution of the divalent metal-containing salt, the gallium-containing salt, and the fermentative or thermophilic bacteria within a range of 5.5 to 8.5.

11. The method of claim 1, wherein the treatment of the divalent metal-containing salt and the gallium-containing salt with the fermentative or thermophilic bacteria to nucleate the divalent metal gallate spinel structure comprises adjusting an $E_h$ of a solution of the divalent metal-containing salt, the gallium-containing salt, and the thermophilic bacteria within a range of 100 mV to -350 mV.

12. The method of claim 5, wherein the zinc gallate spinel structure is a blue phosphor.

13. The method of claim 2, wherein the dopant is at least one selected from the group consisting of Mn, Cr, Eu, Co, Dy, and combinations thereof.

14. The method of claim 6, wherein the doping of the zinc gallate spinel comprises $Co^{2+}$ dopant and the wavelength of light emission ranges from 400 nm to 495 nm.

15. The method of claim 6, wherein the zinc gallate spinel is doped with $Mn^{2+}$ dopant and the wavelength of light emission ranges from 495 nm to 570 nm.

16. The method of claim 15, wherein doping of the zinc gallate spinel structure with $Mn^{2+}$ comprises mixing a manganese salt selected from manganese chloride hydrate ($MnCl_2.xH_2O$), manganese nitrate hydrate ($Mn(NO_3)_2.xH_2O$), manganese sulfate hydrate ($MnSO_4.xH_2O$), manganese iodide ($MnI_2$), manganese bromide ($MnBr_2$), manganese fluoride ($MnF_3$), manganese acetate hydrate ($Mn(CH_3COO)_2.xH_2O$), and manganese carbonate ($MnCO_3$) with said divalent metal-containing salt, gallium-containing salt, and supply of fermentative or thermophilic bacteria in said method of forming a metal gallate spinel structure in claim 1, wherein said divalent metal-containing salt is a zinc-containing salt, to produce said zinc gallate spinel doped with $Mn^{2+}$.

17. The method of claim 6, wherein the zinc gallate spinel is doped with $Cr^{3+}$ or $Eu^{3+}$ and the wavelength of light emission ranges from 570 nm to 750 nm.

18. The method of claim 17, wherein doping of the zinc gallate spinel structure with $Cr^{3+}$ comprises mixing a chromium salt selected from chromium chloride hydrate ($CrCl_3.xH_2O$), chromium nitrate hydrate ($Cr(NO_3)_3.xH_2O$), chromium acetate hydroxide ($(CH_3CO_2)_7Cr_3(OH)_2$), chromium sulfate hydrate ($Cr_2(SO_4)_3.xH_2O$), chromium fluoride hydrate ($GaF_3.xH_2O$), chromium iodide hydrate ($CrI_3.xH_2O$), chromium bromide hydrate ($CrBr_3.xH_2O$), and chromium phosphate hydrate ($Cr(PO_4).xH_2O$), with said divalent metal-containing salt, gallium-containing salt, and supply of fermentative or thermophilic bacteria in said method of forming a metal gallate spinel structure in claim 1, wherein said divalent metal-containing salt is a zinc-containing salt, to produce said zinc gallate spinel doped with $Cr^{3+}$.

19. The method of claim 17, wherein doping of the zinc gallate spinel structure with $Eu^{3+}$ comprises mixing a europium salt selected from europium chloride hydrate ($EuCl_3.xH_2O$), europium fluoride hydrate ($EuF_3.xH_2O$), europium nitrate hydrate ($Eu(NO_3)_3.xH_2O$), europium acetate hydroxide ($(CH_3CO_2)_7Eu_3(OH)_2$), europium bromide hydrate ($EuBr_3.xH_2O$), and europium sulfate hydrate ($Eu_2(SO_4)_3.xH_2O$) with said divalent metal-containing salt, gallium-containing salt, and supply of fermentative or thermophilic bacteria in said method of forming a metal gallate spinel structure in claim 1, wherein said divalent metal-containing salt is a zinc-containing salt, to produce said zinc gallate spinel doped with $Eu^{3+}$.

20. The method of claim 6, wherein the zinc gallate spinel is doped with $Dy^{3+}$ dopant and the wavelength of light emission is in a wavelength ranging from 450 nm to 510 nm, or a wavelength ranging from 560 nm to 610 nm, or a wavelength ranging from 660 nm to 720 nm, or a wavelength ranging from 755 nm to 800 nm.

21. The method of claim 20, wherein doping the zinc gallate spinel structure with $Dy^{3+}$ comprises mixing a dysprosium salt selected from dysprosium chloride hydrate ($DyCl_3.xH_2O$), dysprosium fluoride hydrate ($DyF_3.xH_2O$), dysprosium nitrate hydrate ($Dy(NO_3)_3.xH_2O$), dysprosium acetate hydroxide (($CH_3CO_2$)$_7Dy_3(OH)_2$), dysprosium bromide hydrate ($DyBr_3.xH_2O$), and dysprosium sulfate hydrate ($Dy_2(SO_4)_3.xH_2O$) with said divalent metal-containing salt, gallium-containing salt, and supply of fermentative or thermophilic bacteria in said method of forming a metal gallate spinel structure in claim 1, wherein said divalent metal-containing salt is a zinc-containing salt, to produce said zinc gallate spinel doped with $Dy^{3+}$.

22. The method of claim 2, further comprising annealing of the divalent metal gallate spinel after being doped with a dopant selected from the group consisting of Mn, Cr, Eu, Dy, and combinations thereof.

23. The method of claim 22, wherein the annealing of the divalent metal gallate spinel is conducted at a temperature ranging from 800° C. to 1000° C. for a time ranging from 15 minutes to 2 hours.

24. The method of claim 1, wherein reacting of the divalent metal-containing salt and the gallium-containing salt with the supply of fermentative or thermophilic bacteria is conducted at a temperature ranging from 45° C. to 90° C.

25. The method of claim 1, wherein the divalent metal gallate spinel structure produces white light.

26. A method of forming a structure for emitting white light, the method comprising:
forming a first phosphor of a first doped zinc gallate spinel structure that is nucleated by a first fermentation with a first thermophilic bacteria and first annealing, wherein the first phosphor emits a first wavelength of red light ranging from 570 nm to 750 nm;
forming a second phosphor of a second doped zinc gallate spinel structure that is nucleated by a second fermentation with a second thermophilic bacteria and a second annealing, wherein the second phosphor emits a wavelength of green light ranging from 495 nm to 570 nm;
forming a third phosphor of a third zinc gallate spinel structure that is nucleated by a third fermentation with a third thermophilic bacteria, wherein the third phosphor emits a wavelength of blue light ranging from 400 nm to 495 nm; and
mixing at least the first phosphor, second phosphor and third phosphor to form the structure for emitting the white light.

27. The method of claim 26, wherein at least one of the first annealing and second annealing for forming at least one of the first phosphor or the second phosphor comprises annealing at a temperature ranging from 800° C. to 1000° C. for a time ranging from 15 minutes to 2 hours.

28. The method of claim 26, wherein at least one of the first doped zinc gallate spinel structure, the second doped zinc gallate spinel structure, and the third doped zinc gallate structure comprises a zinc gallate that is nucleated from a mixture of a zinc-containing salt and a gallium-containing salt in the presence of the thermophilic bacteria, wherein reaction between the zinc-containing salt and the gallium-containing salt is not a reduction type reaction.

29. The method of claim 26, wherein the zinc-containing salt is selected from zinc chloride ($ZnCl_2$), zinc bromide ($ZnBr_2$), zinc nitrate hydrate ($Zn(NO_3)_2.xH_2O$), zinc sulfate hydrate ($ZnSO_4.xH_2O$), zinc phosphate ($Zn_3(PO_4)_2$), zinc acetate hydrate (($CH_3CO_2)_2Zn$).$xH_2O$), zinc stearate ($[CH_3(CH_2)_{16}COO]_2Zn$), zinc fluoride ($ZnF_2$), zinc iodide ($ZnI_2$), zinc methoxide ($C_2H_6O_2Zn$), zinc acrylate (($H_2C=CHCO_2)_2Zn$), or combinations thereof, and the gallium-containing salt comprises gallium chloride ($GaCl_3$), gallium chloride ($GaCl_2$), gallium nitrate hydroxide ($GaNO_3.xH_2O$), gallium fluoride ($GaF_3$), gallium iodide ($GaI_3$), gallium bromide ($GaBr_3$), gallium sulfate hydrate ($GaSO_4.xH_2O$), and combinations thereof.

30. The method of claim 26, wherein the second doped zinc gallate spinel structure is doped with $Mn^{2+}$ dopant, wherein the $Mn^{2+}$ dopant is introduced to the zinc gallate by mixing a manganese salt selected from manganese chloride hydrate($MnCl_2.xH_2O$), manganese nitrate hydrate ($Mn(NO_3)_2.xH_2O$), manganese sulfate hydrate ($MnSO_4.xH_2O$), manganese iodide ($MnI_2$), manganese bromide ($MnBr_2$), manganese fluoride ($MnF_3$), manganese acetate hydrate ($Mn(CH_3COO)_2.xH_2O$), and manganese carbonate ($MnCO_3$) with a divalent metal-containing salt, gallium-containing salt, and supply of fermentative or thermophilic bacteria in accordance with the method of forming a metal gallate spinel structure in claim 1, wherein said divalent metal-containing salt is a zinc-containing salt, to produce said zinc gallate spinel doped with $Mn^{2+}$.

31. The method of claim 26, wherein the first doped zinc gallate spinel structure is doped with $Cr^{3+}$ dopant, wherein the $Cr^{3+}$ dopant is introduced to the first doped zinc gallate spinel structure dopant by mixing a chromium salt selected from chromium chloride hydrate ($CrCl_3.xH_2O$), chromium nitrate hydrate ($Cr(NO_3)_3.xH_2O$), chromium acetate hydroxide (($CH_3CO_2)_7Cr_3(OH)_2$), chromium sulfate hydrate ($Cr_2(SO_4)_3.xH_2O$), chromium fluoride hydrate ($GaF_3.xH_2O$), chromium iodide hydrate ($CrI_3.xH_2O$), chromium bromide hydrate ($CrBr_3.xH_2O$), and chromium phosphate hydrate ($Cr(PO_4).xH_2O$) with a divalent metal-containing salt, gallium-containing salt, and supply of fermentative or thermophilic bacteria in accordance with the method of forming a metal gallate spinel structure in claim 1, wherein said divalent metal-containing salt is a zinc-containing salt, to produce said zinc gallate spinel doped with $Cr^{3+}$.

32. The method of claim 26, wherein the first doped zinc gallate spinel structure is doped with $Eu^+$ dopant, wherein the $Eu^{3+}$ dopant is introduced to the first doped zinc gallate spinel structure dopant by mixing a europium salt selected from europium chloride hydrate ($EuCl_3.xH_2O$), europium fluoride hydrate ($EuF_3.xH_2O$), europium nitrate hydrate ($Eu(NO_3)_3.xH_2O$), europium acetate hydroxide (($CH_3CO_2)_7Eu_3(OH)_2$), europium bromide hydrate ($EuBr_3.xH_2O$), and europium sulfate hydrate ($Eu_2(SO_4)_3.xH_2O$) with a divalent metal-containing salt, gallium-containing salt, and supply of fermentative or thermophilic bacteria in accordance with the method of forming a metal gallate spinel structure in claim 1, wherein said divalent metal-containing salt is a zinc-containing salt, to produce said zinc gallate spinel doped with $Eu^{3+}$.

33. The method of claim 28 further comprising forming a fourth phosphor of a fourth doped zinc gallate spinel structure with $Dy^{3+}$ dopant and the wavelength of light emission for the fourth doped zinc gallate spinel is in a wavelength ranging from 450 nm to 510 nm, or a wavelength ranging from 560 nm to 610 nm, or a wavelength ranging from 660 nm to 720 nm or a wavelength ranging from 755 nm to 800 nm.

34. The method of claim 33, wherein doping of the zinc gallate spinel structure with $Dy^{3+}$ comprises mixing a dysprosium salt selected from dysprosium chloride hydrate ($DyCl_3.xH_2O$), dysprosium fluoride hydrate ($DyF_3.xH_2O$), dysprosium nitrate hydrate ($Dy(NO_3)_3.xH_2O$), dysprosium acetate hydroxide ($(CH_3CO_2)_7Dy_3(OH)_2$), dysprosium bromide hydrate ($DyBr_3.xH_2O$), and dysprosium sulfate hydrate ($Dy_2(SO_4)_3.xH_2O$) with a divalent metal-containing salt, gallium-containing salt, and supply of fermentative or thermophilic bacteria in accordance with the method of forming a metal gallate spinel structure in claim 1, wherein said divalent metal- containing salt is a zinc-containing salt, to produce said zinc gallate spinel doped with $Dy^{3+}$.

35. A white light emitting structure comprising:
 a first zinc gallate spinel doped with chromium or europium that provides a red light emitting phosphor;
 a second zinc gallate spinel doped with manganese that provides a green light emitting phosphor;
 a third zinc gallate spinel that provides a blue light emitting phosphor; and
 a transparent substrate, wherein the first zinc gallate spinel, the second zinc gallate spinel, and
 the third zinc gallate spinel are distributed as a mixture of said first, second, and third zinc gallate spinels on or within the transparent substrate.

36. The white light emitting structure of claim 35, wherein said mixture is a homogeneous mixture.

* * * * *